US005993851A

United States Patent [19]

Foldvari

[11] Patent Number: 5,993,851

[45] Date of Patent: Nov. 30, 1999

[54] METHOD FOR PREPARING BIPHASIC MULTILAMELLAR LIPID VESICLES

[75] Inventor: Marianna Foldvari, Saskatoon, Canada

[73] Assignee: PharmaDerm Laboratories, Ltd., Saskatchewan, Canada

[21] Appl. No.: 09/042,097

[22] Filed: Mar. 13, 1998

Related U.S. Application Data

[62] Division of application No. 08/872,068, Jun. 10, 1997, which is a continuation of application No. 08/507,923, Jul. 27, 1995, abandoned, which is a continuation-in-part of application No. 08/098,102, Jul. 28, 1993, abandoned.

[51] Int. Cl.[6] ..................... A61K 9/127

[52] U.S. Cl. ..................... 424/450; 424/1.21; 424/9.321; 424/9.51; 424/417; 424/402.2; 264/4.1; 264/4.3; 264/4.32; 264/4.6

[58] Field of Search ..................... 424/450, 1.21, 424/9.321, 9.51, 417; 428/402.2; 264/4.1, 4.3, 4.32, 4.6; 514/937–943

[56] References Cited

U.S. PATENT DOCUMENTS

| | | |
|---|---|---|
| 4,311,707 | 1/1982 | Birnbaum et al. . |
| 4,485,054 | 11/1984 | Mezei et al. . |
| 4,522,803 | 6/1985 | Lenk et al. . |
| 4,687,661 | 8/1987 | Kikuchi et al. . |
| 4,761,288 | 8/1988 | Mezei . |
| 4,897,269 | 1/1990 | Mezei . |
| 4,911,928 | 3/1990 | Wallach . |
| 5,030,453 | 7/1991 | Lenk et al. . |
| 5,169,637 | 12/1992 | Lenk et al. . |
| 5,234,767 | 8/1993 | Wallach . |
| 5,260,065 | 11/1993 | Mathur et al. . |
| 5,260,086 | 11/1993 | Mathur et al. . |

FOREIGN PATENT DOCUMENTS

| | | |
|---|---|---|
| 1143656 | 3/1983 | Canada . |
| 2018825 | 6/1990 | Canada . |
| 1280975 | 3/1991 | Canada . |
| 2024804 | 3/1991 | Canada . |
| 2018825 | 12/1991 | Canada . |
| 0130577 | 1/1985 | European Pat. Off. . |
| 0292403 | 11/1988 | European Pat. Off. . |
| 90/12565 | 11/1990 | WIPO . |
| 91/01719 | 2/1991 | WIPO . |
| 92/06676 | 4/1992 | WIPO . |
| 92/19243 | 11/1992 | WIPO . |
| 93/00894 | 1/1993 | WIPO . |

OTHER PUBLICATIONS

Uekama, K. et al., "Improved Transdermal Delivery of Prostaglandin $E_1$ Through Hairless Mouse Skin: Combined Use of Carboxymethyl–ethyl–β–Cyclodextrin and Penetration Enhancers," *Communications.* 119–121 (1991).

Watkinson, A.C. et al., "Aspects of the Transdermal Delivery of Prostaglandins," *International Journal of Pharmaceutics.* 74 229–236 (1991).

Adam C. Watkinson et al., "Aspect of the Transdermal Delivery of Prostaglandins": *International Journal of Pharmaceutics*, 74 (1991); pp. 229–236.

Kaneto Uekama et al., "Improved Transdermal Delivery of Prostaglandin $E_1$ through Hairless Mouse Skin: Combined Use of Carboxymethyl–ethyl–β–Cyclodextrin and Penetration Enhances"; Communications (1991): pp. 119–121.

*Primary Examiner*—Gollamudi S. Kishore
*Attorney, Agent, or Firm*—Judy M. Mohr; Dehlinger & Associates

[57] ABSTRACT

A biphasic multilamellar lipid vesicle comprising a plurality of spaced apart lipid bilayers that include a liposome-forming component and optionally a biologically active agent entrapped within the lipid bilayers. The lipid vesicle also comprises peripheral aqueous solution compartments formed between the lipid bilayers and a central lipophilic core compartment substantially at the center of the multilamellar lipid vesicle.

22 Claims, 3 Drawing Sheets

19 17 20 16 15 18 21 9 12 13 14 11 10

METHOD FOR PREPARING BIPHASIC MULTILAMELLAR LIPID VESICLES

This application is a divisional of now-allowed U.S. patent application Ser. No. 08/872,068, filed Jun. 10, 1997, which is pending, which is a continuation of now-abandoned U.S. patent application Ser. No. 08/507,923, filed Jul. 27, 1995, now abandoned, which is a continuation-in-part of now-abandoned U.S. patent application Ser. No. 08/098,102, filed Jul. 28, 1993, abandoned. All three applications are incorporated herein by reference.

BACKGROUND OF THE INVENTION

Liposomes are microscopic vesicles composed of a single phospholipid bilayer or a plurality of concentric phospholipid bilayers which enclose aqueous phases. These vesicles can serve as drug carriers for hydrophobic as well as hydrophilic substances, including various drug molecules and peptides. Liposomes are prepared mainly from phospholipids of different headgroups and chain lengths, and cholesterol. Due to physicochemical similarities with cell membranes, liposomes are biocompatible, biodegradable and non-toxic vehicles for drug molecules.

U.S. Pat. Nos. 4,911,928 and 5,234,767, both to Wallach, describe lipid vesicles as substantially spherical structures made of materials having high lipid content, e.g. surfactant or phospholipid; (see column 1 lines 25 to 27 of U.S. Pat. No. 5,234,767). The lipids of these spherical vesicles are said to be organized in the form of lipid bilayers. The lipid bilayers encapsulate an aqueous volume which is either interspersed between multiple onion-like shells of lipid bilayers (forming multilamellar lipid vesicles or "MLV") or the aqueous volume is contained within an amorphous central cavity. Mention is also made of large unilamellar vesicles ("LUV") generally having a diameter greater than about 1 $\mu$m, small unilamellar vesicles ("SUV") generally having a diameter less than about 0.2 $\mu$m and paucilamellar lipid vesicles ("PLV") which have about 2 to about 8 or 10 peripheral bilayers. Although Wallach says that PLV's can be considered to be a sub-class of the MLV's, he says that electron micrographs confirm that the paucilamellar lipid vesicles are distinct from the LUV's and the classic MLV's; (U.S. Pat. No. 4,911,928 column 3, lines 29 to 31) This invention is not concerned with PLV's but is concerned with classic MLV's having substantially more lipid bilayers than PLV's, the MLV's having at least about 15 lipid bilayers, normally more than about 30 and frequently over 100.

Liposomes are prime candidates for the systemic as well as topical delivery of drugs. Several studies showed that liposome encapsulation advantageously alters the pharmacokinetic fate of the drug after topical application. The first experimental evidence that liposomes may penetrate into the skin and deposit within the dermis was obtained recently by using a novel small particle-size electrondense marker (colloidal iron), which can be efficiently encapsulated into liposomes of various sizes and compositions, and can be easily identified in cells and tissues by electron microscope.

However, current liposome technology suffers from a number of important drawbacks that has prevented its widespread use in dermal applications and in systemic delivery. Hence, liposome formulations present consistency problems for skin applications that have so far been solved by either adding viscosity-increasing agents such as cellulose derivatives to the pharmaceutical composition that contains the liposomes as active ingredient or by using higher concentrations of phospholipids in the preparation of the liposomes.

The addition of viscosity-increasing agents to the final liposome composition usually dilutes the product but, more importantly, these agents were shown to decrease the release of encapsulated drug from the liposomes; Foldvari, et al. (1993) J. Controlled Release 27; 193–205. Also, viscosity-increasing agents have a detrimental effect on the integrity of the liposomes. With regard to phospholipids, lipids, they are the main and also the most expensive liposome-forming ingredient. Their use as a viscosity-increasing agent is therefore not economically practical.

Two potential applications of the liposome technology described herein are the treatment of sexual dysfunction and the treatment of genital warts.

1. Sexual Dysfunction

Impotence, the partial or complete inability of the male to perform the sexual act or to achieve orgasm, may be psychogenic and/or organic in nature. Initially, psychogenic etiology was considered to account for 95 percent of cases of impotence but it is now apparent that organic factors are almost invariably involved in cases of impotence. Thus, impotence is best characterized as either of predominantly organic or predominantly psychogenic etiology.

Impotence is a socially crippling disease. It detracts from the patient's self esteem and in some cases his ability to interact with others. Current therapy modes include psychotherapy, microsurgery (to restore compromised vascular supply), implantation of penile prosthesis and pharmacotherapy.

Numerous agents have been employed in the therapy of impotence. Hormonal manipulation, such as replacement androgen therapy, has been used. However, patients with organic impotence are rarely candidates for hormonal manipulation. Thus, this mode of therapy should be strictly limited to cases in which endocrine deficiencies are established. Furthermore, in about 50 percent of patients with an endocrinopathy, a psychogenic etiology can be shown to be the predominant factor in erectile difficulties. Therefore, in the vast majority of impotent men, vascular and neurologic factors are the underlying causes. The most commonly used treatment for these patients is the implantation of penile prostheses. The invasive nature of this technique, coupled with the increasing evidence of mechanical failure, surgical complications, or infection has again focused attention on the development of pharmacological agents with a potential for improving the libido and quality of erections. Several agents have been tested e.g. bromocriptine, glyceryl trinitrate, zinc, oxytocin, yohimbine and nitroglycerin. Intracorporeal injection of vasoactive agents is now considered the treatment of choice for many patients with organic impotence (Kattan et. al., 1991).

Injection of papaverine, a smooth muscle relaxant, or a combination of papaverine and phentolamine (an a-adrenergic blocker) directly into the corpus cavernosum (either of the two erectile columns of the dorsum of the penis) has been shown to be an effective therapy in impotence. Recently, intercavernosal injections of prostaglandin $E_1$ (alprostadil), a naturally occurring chemical derived from dihomo-gammalinolenic acid (20:3∞6) was discovered to also induce erection.

Injection of prostaglandin $E_1$ results in vasodilation, with increased arterial inflow and decreased venous outflow by occlusion of draining venules, probably through relaxation of corporal smooth muscle. Due to its potent relaxant effect on vascular smooth muscle, prostaglandin $E_1$ is used to maintain the patency of the ductus arteriosus in the neonate. This is the only currently approved (FDA) indication for prostaglandin $E_1$. The effect of prostaglandin $E_1$ on erectile dysfunction is known to be dose dependent.

Prostaglandin $E_1$ ($PGE_1$), a potent relaxant of the vascular smooth muscle, has been shown to be effective and safe in the treatment of impotence by increasing arterial inflow through vasodilatation and decreasing venous outflow by the occlusion of draining venules due to relaxation of corporal smooth muscle. As opposed to other previously used drugs such as papaverine or phentolamine, $PGE_1$ is not as frequently associated with the common side effects e.g. priapism, plaques at the injection site and liver function abnormalities, therefore it is clinically more acceptable. $PGE_1$ is usually self-injected into the corpus cavernosum through the lateral aspect of the shaft of the penis. This type of administration, however, is associated with penile discomfort, pain at the injection site and the inconvenience of application prior to intercourse. Topical application of $PGE_1$ would be an ideal route of administration, however, the drug itself (without a delivery system) cannot penetrate the skin in adequate concentration and would be metabolized within the skin very quickly before reaching the underlying tissues.

2. Genital Warts

It is estimated that condylomata acuminata contributes to 1.3–1.4 million office visits per year in the United States, representing a 580% increase between 1966 and 1983 (Center for Disease Control, 1983). Condylomata acuminata is caused by the human papillomavirus (HPV) and it is one of the most commonly diagnosed viral sexually transmitted diseases. More than 50 types of HPV has been categorized and new types are constantly being identified. Certain subsets of HPV (mostly type 16 and 18) has been shown to be associated with malignant tumors of the ano-genital tract, respiratory tract and the skin.

Conventional therapy for genital warts has included podophyllin, cryotherapy, trichloroacetic acid, electrical cautery, laser ablation and conventional surgery, and has been directed primarily at visible lesions. Recurrences after therapy for HPV infections is very common, which could be due to incomplete eradication of the virus since the presence of residual virus in normal-appearing tissue has been demonstrated.

Interferon has activity against papillomaviruses, and cures infected cells by eliminating extrachromosomal viral DNA. Systemic application (i.m. injection) of interferon alpha in patients with genital warts was shown to be fairly successful, however it is associated with various side effects such as fever, myalgias, headache, nausea, fatigue. Intralesional IFN treatment appears to be a more promising approach for visible lesions, but it is not suitable for latent or subclinical infections. Initially highly positive results (90% complete response) were reported with topical natural leukocyte IFN. Vesterinen et al. reported colposcopic remission in five out of eight patients with vaginal flat condylomas treated with a potent topical IFN cream. However, in spite of the improvement of clinical appearance, the cytology remained positive in all cases and two responding patients had recurrences in two months.

SUMMARY OF THE INVENTION

I have now found novel multilamellar lipid vesicles that are superior to the previously known liposomes with regard to encapsulation efficiency, uniformity of encapsulation and consistency. This latter characteristic enables the novel vesicles to be used in dermal applications either with lesser amounts of viscosity increasing agents or entirely without viscosity increasing agents, such as the abovementioned cellulose derivatives.

Accordingly, in one aspect the present invention provides biphasic multilamellar lipid vesicles suitable for use as a vehicle for administration of a biologically active material and having more than about 15 lipid bilayers surrounding a core compartment, wherein:

(1) the lipid bilayers consist essentially of a phospholipid, a glycolipid, a ceramide or a mixture thereof, optionally up to about 10 per cent by weight of a fatty substance to enhance the strength of the lipid bilayers and optionally up to about 5 per cent of a cutaneous or percutaneous penetration enhancer to enhance penetration of biologically active material into or through the skin, the percentages being based on the weight of the final product;

(2) the core compartment of the lipid vesicles is occupied by an emulsion of lipophilic dispersed phase and water as continuous phase;

(3) the lipophilic phase of the emulsion contains a biologically active material or a consistency enhancer, or contains both a biologically active material and a consistency enhancer;

(4) the space between adjacent lipid bilayers is occupied by an aqueous phase.

In a modification of the invention there are provided multilamellar lipid vesicles containing an interferon, preferably interferon alpha, and having more than about 15 lipid bilayers surrounding a core compartment, wherein:

(1) the lipid bilayers consist essentially of a phospholipid, a glycolipid, a ceramide or a mixture thereof, optionally up to about 10% by weight of a fatty substance to enhance the strength of the lipid bilayers and optionally up to about 5% by weight of a surfactant to enhance penetration of the interferon into or through the skin, the percentages being based on the weight of the product;

(2) the core compartment of the lipid vesicles is occupied by an aqueous phase;

(3) the space between adjacent lipid bilayers is occupied by an aqueous phase; and (4) an interferon is dissolved in the aqueous phase. In this modification of the invention it is not essential that the vesicles contain an emulsion in the core compartment. This possibility is within the scope of this modification of the invention, however. The core compartment can be occupied by an emulsion composed of an aqueous continuous phase and a consistency enhancer as dispersed oil phase.

DESCRIPTION OF THE PREFERRED EMBODIMENTS

Figure 1:
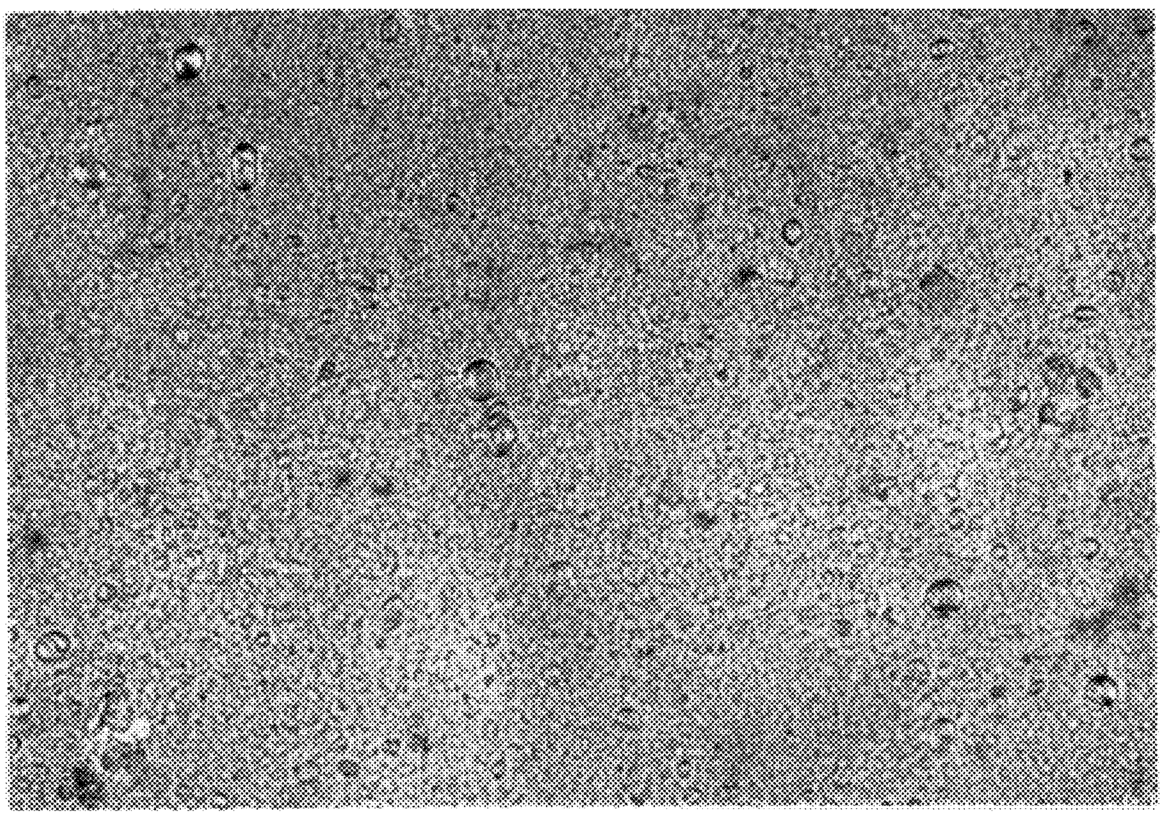

The multilamellar lipid vesicle can incorporate various ingredients in one or more of three regions in each vesicle. These regions are (i) the central core compartment, (ii) the spaces between adjacent lipid bilayers, sometimes referred to herein as the peripheral compartments, and (iii) the spaces between two layers of a lipid bilayer; i.e. within the bilayer. As the interior of the lipid bilayer is lipophilic, only lipophilic substances can be present within the bilayers.

By a biphasic vesicle is meant a vesicle whose central core compartment is occupied by an ingredient that is in two phases, i.e., an emulsion composed of an aqueous continuous phase and a dispersed hydrophobic, lipophilic or oil phase. The peripheral compartments may also be occupied by the emulsion.

The vesicle of the invention has a central core compartment that contains an emulsion with oil as the dispersed phase. Water-soluble ingredients can be dissolved in the water phase of the emulsion. Oil-soluble ingredients can be dissolved in the oil droplets of the emulsion, or can be emulsified. The central core compartment is surrounded by a multitude, at least about fifteen and normally many more, substantially concentric spherical lipid bilayers. Between each adjacent pair of lipid bilayers is a space that is occupied by water. In that water there can again be emulsified oil droplets or emulsified lipophilic substances or both. Water-soluble substances can be dissolved in the water and lipophilic substances can be dissolved in emulsified oil droplets or be emulsified as dispersed phase in the water. Lipophilic ingredients can be incorporated actually within the lipid bilayer. (For the purpose of this specification "biologically active material, agent or compound" shall mean any material, agent or compound that has a pharmacological, pharmaceutical or cosmetic effect.) A composition of lipid vesicles in accordance with the invention and containing no biologically active material can be of value, for example, as a moisturizing cream.

Incorporation of lipophilic substances in the central core compartment of the multilamellar lipid vesicle is accomplished through a lipophilic substance-in-water emulsion in the form of one or more droplets whose surface bears a surfactant. It should be appreciated that the vesicles are so small that it is possible that there may be only one oil droplet present in the emulsion that is contained in the core compartment of a vesicle.

Although glycolipids, phospholipids and ceramides have surfactant properties, it is desirable that surfactants other than these materials should be used to emulsify the oil phase of the emulsion, and that the oil droplets shall be surrounded by surfactant, i.e., shall be emulsified, before they encounter the phospholipid, glycolipid or ceramide. If this is not the case the phospholipid, glycolipid or ceramide may itself act as the emulsifying surfactant in a single layer of surfactant. If this occurs the phospholipid, glycolipid or ceramide may not form the lipid bilayers that characterize vesicles, so that there is formed only an emulsion but no lipid vesicles. The surfactant is preferably a primary cationic emulsifier such as linoleamidopropyl PG-Dimonium chloride phosphate (PEFA). Other suitable surfactants include cocamidopropyl PG-dimonium chloride phosphate and stearamido PG-dimonium chloride phosphate.

Coating the oil droplets or solid/semisolid lipophilic ingredients with a suitable surfactant can be followed, if necessary, by a reduction of the size of the droplets, preferably to below about 0.5 $\mu$m, using a high pressure homogenizer. This procedure provides a milky solution which can be used as aqueous phase in the formation of liposomes.

Preferred lipophilic substances that can be incorporated in the central core of the multilamellar lipid vesicles of the present invention include oils and solid or semisolid lipophilic consistency enhancers in which biologically active lipophilic compounds can be incorporated.

A preferred process for the preparation of multilamellar lipid vesicles of the invention comprises forming a lipid phase melt by mixing the phospholid, glycolipid or ceramide and preferably a fatty substance adapted to enhance the strength of lipid bilayers with a pharmaceutically acceptable hydrophilic solvent other than water and optionally a biologically active compound to produce an anhydrous proliposome gel in the form of a stable lipid phase melt. A lipophilic substance-in-water emulsion, optionally comprising a biologically active compound, is then added to the proliposome gel and the multilamellar lipid vesicles are recovered.

The lipophilic substance-in-water emulsion is prepared by dissolving surfactant and any water-soluble components in water and adding the oil phase, i.e., the lipophilic substance, to the water. They can be mixed in a homogenizer, for example, for a suitable period of time, say 5 to 30 minutes. The oil phase preferably comprises at least one component selected from the group consisting of an oil and a solid or semisolid lipophilic consistency enhancer.

Multilamellar lipid vesicles within the scope of the present invention can be used particularly for topical applications. When the preferred process for making vesicles is used the peripheral compartments comprise at least traces of a pharmaceutically acceptable hydrophilic solvent and the obtained multilamellar lipid vesicles are devoid of traces of toxic organic solvents, such as chloroform or methanol, which are usually employed in conventional liposome-forming techniques for dissolving the liposome-forming component. It is noted that the vesicles are composed entirely, or almost entirely, of materials that occur in nature and are compatible with skin.

Optionally, the lipid bilayers can further comprise at least one cutaneous or percutaneous penetration enhancer agent entrapped within the lipid bilayers or adsorbed on the surface thereof, to enhance penetration of any biologically active material into or through the skin. Preferred penetration enhancer agents include methyl salicylate and fatty acylated amino acids such as monolauroyllysine and dipalmitoyllysine.

Also within the scope of the present invention is a liposome composition comprising a population of biphasic multilamellar lipid vesicles, as described above. The multilamellar lipid vesicle population has a substantially uniform size distribution, preferably ranging between 0.1 and 10 $\mu$m, while being substantially devoid of aggregated or fused liposomes.

Also within the scope of the invention is a method for the treatment of erectile dysfunction. This method comprises topically administering to a patient in need thereof an effective amount of a liposome composition comprising a population of multilamellar lipid vesicles having a prostaglandin, preferably $PGE_1$, entrapped within the vesicles.

The invention also relates to a method for the treatment of papillomavirus infections. The method comprises topically administering to a patient in need thereof an effective amount of a liposome composition comprising a population of multilamellar lipid vesicles and interferon alpha entrapped within the vesicles.

Also within the scope of the present invention is the use of a topical liposome composition for the application of $PGE_1$ in the treatment of impotence. The liposome composition comprises a population of multilamellar lipid vesicles containing $PGE_1$.

Also within the scope of the present invention is the use of multilamellar lipid vesicles in the preparation of a medicament for the treatment of papillomavirus infections.

Also, the formulation of liposomal IFN has contributed to the development of an effective form of topical interferon, and offers the advantage of treating latent HPV infections as well as visible genital warts. The formulation of liposomal IFN could be administered by the patients at home without the need for multiple painful local or i.m. injections.

The multilamellar lipid vesicles of the present invention have shown high encapsulation efficiency of hydrophilic, lipophilic and oil-like active ingredients. The simplicity of the preferred method by which the vesicles can be prepared allows production on a large scale.

A population of multilamellar lipid vesicles in accordance with the invention may have the consistency of a cream, and can therefore be used as such. In the past liposomal formulations have not displayed the consistency of a cream, and it has been necessary to incorporate them in a cream-base or gel matrix to obtain a preparation that is suitable for topical application. With the multilamellar lipid vesicles of the invention use of a cream base or gel matrix may not be necessary, although of course preparations composed of vesicles of the invention and a cream base or gel matrix are not outside the scope of the invention.

With the preferred process a more physically stable liposome composition is obtained. A more uniform liposome-size distribution is achieved while aggregation and fusion of liposomes is reduced. Furthermore, the consistency of the final liposome composition is also substantially improved. It has also been demonstrated that encapsulation efficiency is higher or at least as good as the more conventional solvent evaporation method. It would also appear that encapsulation of ingredients is more reproducible and this is indicated by smaller standard deviations.

Other important features of the liposomal composition of the present invention include the possibility of encapsulation of one or more (coencapsulation) of a wide range of active ingredients with different physicochemical properties. For example, lipid compounds which are not soluble in organic solvents can now be used for liposome construction.

The multilamellar lipid vesicles developed using the preferred process of the present invention can be used to deliver oil droplets containing solubilized lipophilic drugs or oily plant extracts. The present invention also allows the encapsulation of lipophilic solid/semisolid consistency enhancers into the central core compartment of the multilamellar lipid vesicles. This provides enhanced viscosity for the final product and reduces or eliminates the requirements to add viscosity-increasing agents to the final liposome preparation.

IN THE DRAWINGS

Figure 2A:
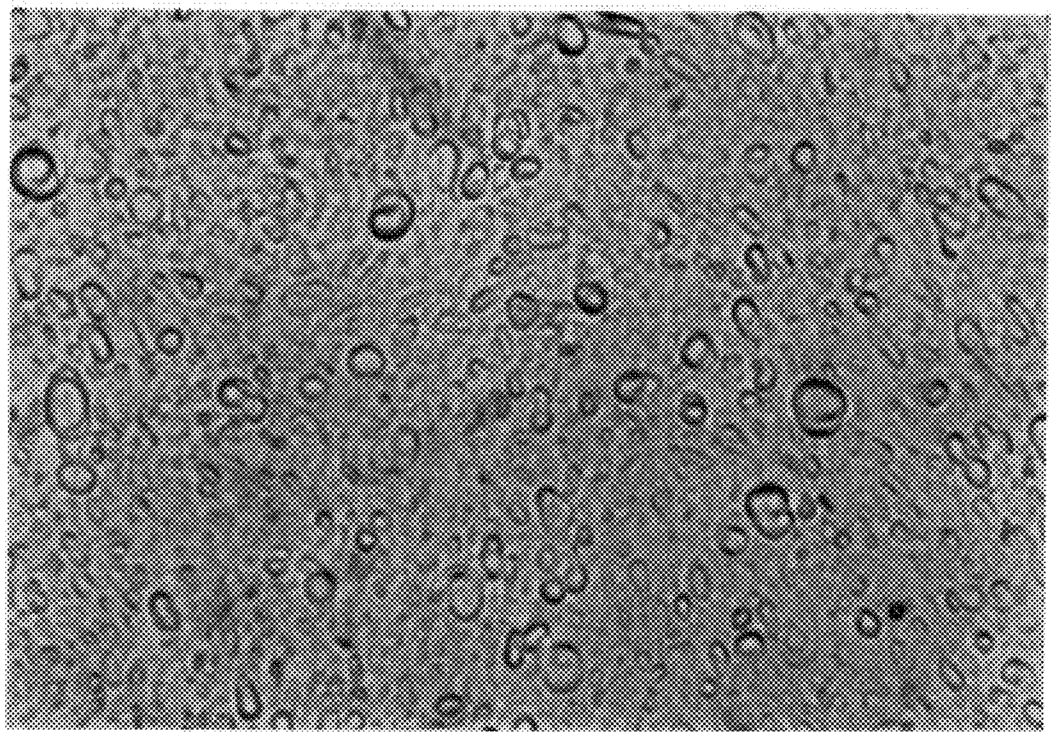

FIG. 1 is a scanned image of multilamellar lipid vesicles of the invention, prepared using the anhydrous plastic proliposome gel method;

FIG. 2*a* is a scanned image of multilamellar liposomes prepared by the preferred method of this invention using "anhydrous plastic proliposome-gel" ('melt' or 'fusion') method.

Figure 2B:
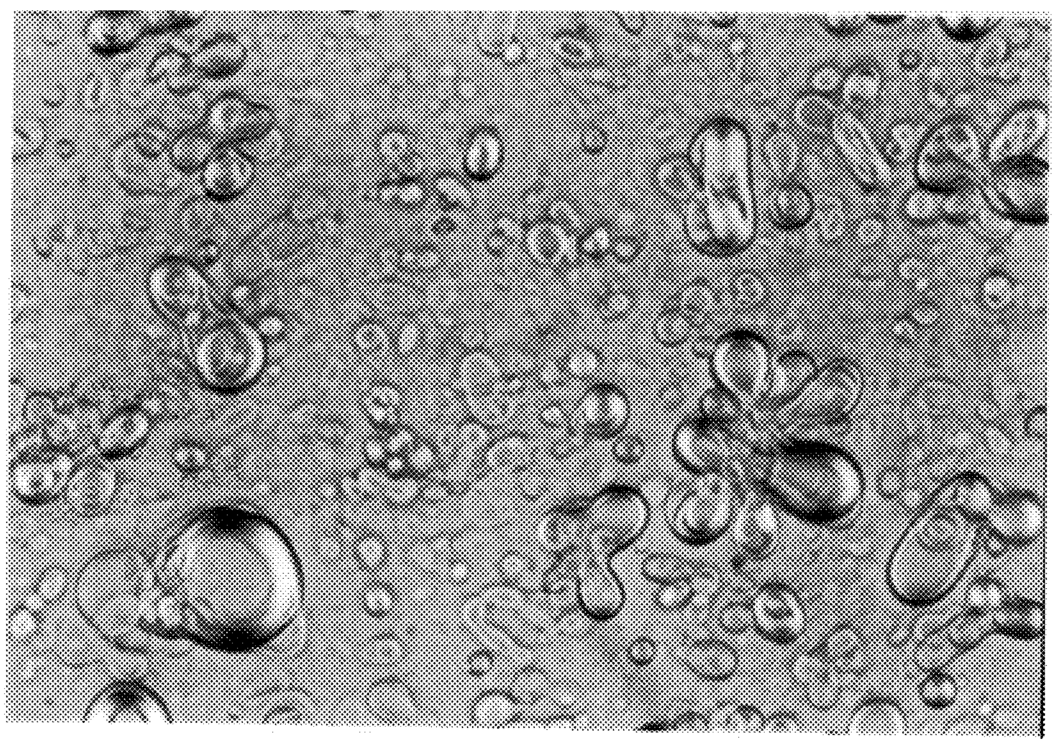

FIG. 2*b* is a scanned image of multilamellar liposomes the same composition as in 2*a*) prepared with solvent evaporation method.

Figure 3:
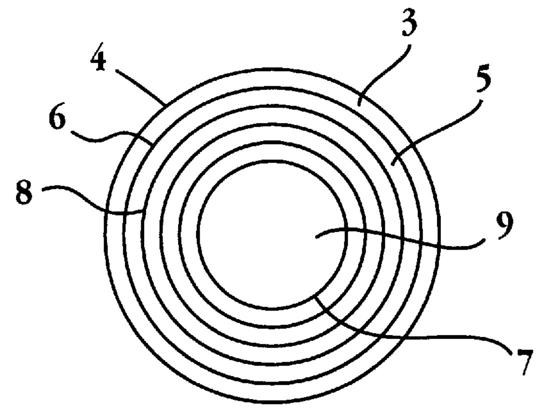
Figure 4:
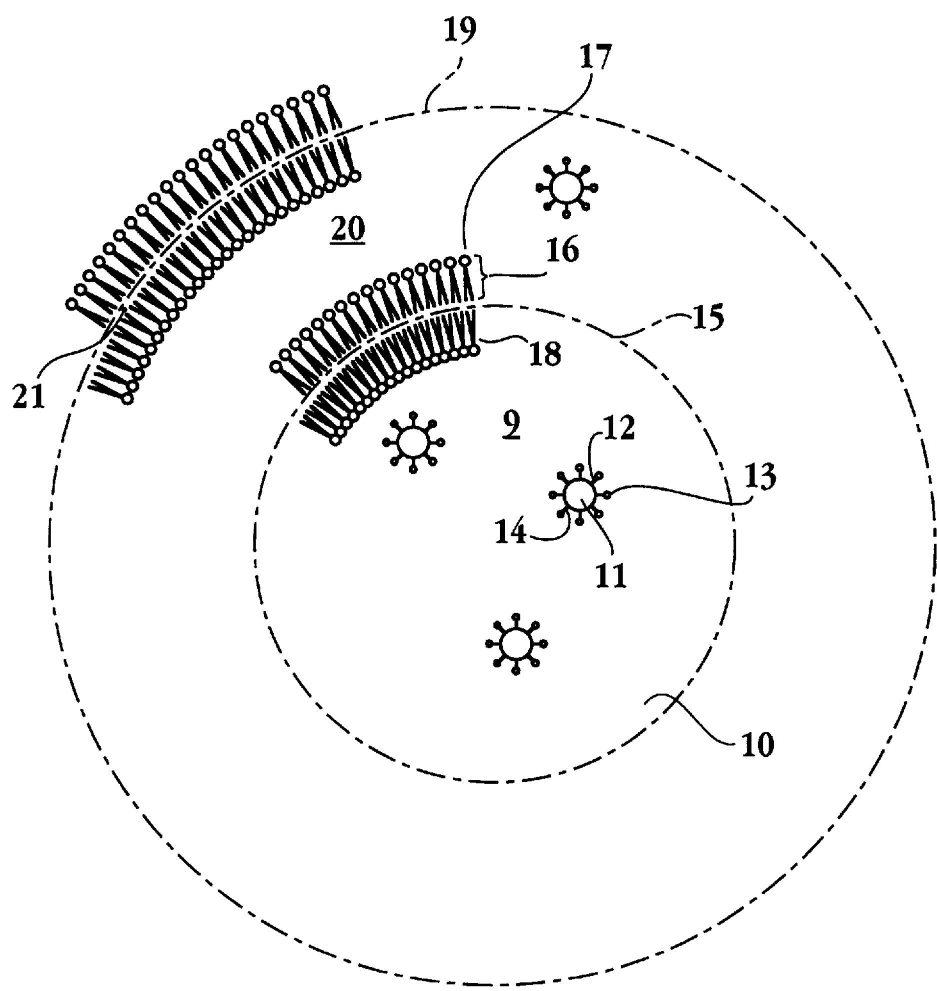

FIG. 3 is a schematic sectional view of a biphasic MLV with a central aqueous emulsion core, and FIG. 4 is an enlarged portion of the MLV of FIG. 3.

DETAILED DESCRIPTION OF THE INVENTION

The invention relates to liposomal compositions for oral and topical use, particularly for the dermal and transdermal delivery of biologically active compounds including, for example, prostaglandins, proteins, anti-viral agents, anaesthetics, vitamins, herbal extracts and antiinflammatory agents. The liposome compositions of the present invention can be used for the topical administration of biologically active compounds to hairy or hairless areas of the skin. They can also be used in mucus membranes for nasal, buccal, ocular, otic, vaginal and urethral administration. The liposome compositions can also be used for localized (intradermal and intramucosal) or systemic (transdermal or transmucosal) delivery as well as in subcutaneous or intracutaneous injection for slow release depot in or beneath the skin.

A preferred method of preparing a multilamellar lipid vesicle of the invention is as follows. An oil and a consistency enhancer are admixed. Separately, water and a surfactant are admixed. A water-soluble antimicrobial agent, for example methyl paraben or propylparaben, can also be dissolved in the water. These are heated gently, say to about 70° C., and then admixed and homogenized with the oil and consistency enhancer. This results in formation of an emulsion with water as the continuous phase and the oil and consistency enhancer as the dispersed phase. It is desirable that the oil droplets shall be less than about 1 $\mu$m, especially less than about 0.5 $\mu$m, in diameter and if necessary the emulsion can be subjected to additional shear or to sonification to reduce the size of the droplets.

Separately there is prepared an anhydrous proliposome gel by admixing the phospholipid, glycolipid or ceramide and a pharmaceutically acceptable hydrophilic solvent, preferably propylene glycol, and heating them to form a melt. In the melt there may also be incorporated a material to enhance the strength of the lipid bilayers, for example cholesterol, a material to enhance penetration, for example monolauroyllysine and a material to impart a charge to the lipid bilayers, for example stearic acid. A small amount of an antioxidant, for example ascorbyl palpitate, can be incorporated in the melt. The aqueous emulsion is added to the melt and the various components are subjected to gentle agitation which results in formation of the desired multilamellar lipid vesicles having in the central core compartment an aqueous emulsion containing the oil and consistency enhancer as the dispersed phase. A water-soluble biologically active material can be incorporated in solution in the aqueous phase of the emulsion. An oil-soluble biologically active material can be dissolved in the oil, before the emulsion is prepared, and incorporated into the vesicles in the emulsified oil droplets. Additionally or alternatively, an oil-soluble or solid or semi-solid biologically active material can be included in the anhydrous proliposome gel and incorporated into the vesicles in the lipid bilayers.

Formation of an anhydrous plastic proliposome gel

A liposome-forming component and other necessary excipients are melted with a pharmaceutically acceptable hydrophilic solvent such as propylene glycol. In addition, the following (or other similar) propylene glycol based extracts can be used in place of the propylene glycol for mixing with the liposome forming component to produce an anhydrous proliposome gel: lavender, sage, rosemary, roman chamomile, carrot, myrrh, pot marigold, elder, arnica, eucalyptus, witch hazel, devil's claw, meadow sweet, willow, silver birch, rose hips, German chamomile, horse chestnut, cypress, incense, benjamine, thyme, gingko biloba and yarrow.

The expression "liposome-forming component" designates the substance or substances used as major component of the lipid bilayers. Typical liposome-forming components include glycolipids, lecithins, phospholipids, ceramides or mixtures thereof which are used as a primary ingredient in the formation of the lipid bilayer. However, other natural and synthetic compounds having the required amphipatic character can be incorporated with the phospholipid, glycolipid or ceramide, replacing some of these expensive materials, provided that the essential character of the lipid bilayers is not adversely affected. The choice of the appropriate materials is within the knowledge of the person skilled in the art. Examples include phosphatidylethanolamine, lysolecithin, lysophosphatidylethanolamine, phosphatidylserine, phosphatidylinositol, sphingomyelin, cardiolipin, phosphatidic acid and the cerebrosides, ether lipids and phytanols.

The liposomal formulations of the present invention preferably contain saturated and/or unsaturated phospholipids, more preferably phosphatidylcholine, lysophosphatidylcholine, phosphatidylserine, phosphatidylethanolamine, glycolipids and ceramides. The phospholipids are preferably in combination with a penetration enhancing agent such as monolauroyllysine, dipalmitoyllysine or methyl salicylate to achieve predominantly transdermal delivery potential.

A "fatty substance" can be used to enhance the strength of the lipid bilayers. Examples of useful fatty substances include steroids such as cholesterol, coprostanol, cholestanol and cholestane and long chain fatty acids ($C_{16}$ to $C_{22}$), especially saturated ones such as stearic acid. In addition to enhancing strength of the lipid bilayer, acids impart a negative charge. Saturated or unsaturated acids can be used. Other fatty substances that can be used include $C_{16}$–$C_{22}$ fatty amines, fatty acylated proteins, fatty acylated peptides, fatty acylated PEG and derivatives. These fatty substances are incorporated with the abovementioned liposome-forming components and improve physical stability and appearance of the product.

The hydrophilic solvent is used as a plasticizer of the liposome-forming component and an aid to prepare a uniform melt. Examples of hydrophilic solvents include but are not restricted to propylene glycol, glycerol, polyethylene glycol having a molecular weight ranging between 300 and 8000, ethanol, and mixtures thereof. The resulting melt can be described as being an anhydrous plastic proliposome gel. This anhydrous plastic proliposome gel contains all the lipid phase ingredients and can be prepared and stored in advance in large quantities. It is a semisolid material with a homogenous consistency.

Formation of the multilamellar lipid vesicles

Hydrophilic ingredients such as penetration enhancers, preservatives and the like, are prepared separately as an aqueous solution, which forms the continuous phase of an emulsion. This is added to the lipid phase melt, previously heated to the appropriate melting temperature that can range from 40° C. to 80° C., and vigorously mixed by any given technique which allows the achievement of the desired product size. Examples of mixing techniques include vortexing or propeller mixing. At this stage, it is also possible to incorporate (dissolve) solid biologically active agents that will be entrapped within the lipid bilayers.

This procedure is suitable for the preparation of various amounts of topical liposomal product. If vortex mixing is used as the agitation, up to about 20 g of the product can be prepared. If a laboratory scale propeller mixer is used, up to about 2000 g of the product can be made. This formulation procedure can also be adapted for large scale manufacturing. Hence, the propeller mixing technique can be directly scaled up by geometrically increasing the size of the vessel and the diameter of the propeller mixer. However, as the vessel size increases, the preferred set up would be a combination mixer i.e a high intensity mixer with propeller mixer and a scraped surface agitator. The aqueous phase is pumped from tank A to tank B containing the anhydrous plastic proliposome gel at the required temperature and mixed. This procedure is suitable for the production of any topical liposomal product on a large scale.

Liposomal compositions can be prepared with the multilamellar lipid vesicles of the present invention by using appropriate pharmaceutical additives. For example, it might be required to add viscosity increasing agents to the final liposome preparation. The addition of other pharmaceutically acceptable compounds is within the purview of the person skilled in the art.

Characteristics of the final multilamellar lipid vesicle product

A schematic representation of a multilamellar lipid vesicle prepared in accordance with the process described above is shown at FIG. 3. The multilamellar lipid vesicle, generally designated by reference numeral 2, is made of a series of spaced apart lipid bilayers 4, 6 and 8 which define a series of peripheral aqueous solution compartments 3 and 5. The smallest lipid bilayer 7 defines in its center a central core compartment 9. Although only 6 lipid bilayers are shown, it should be appreciated that the figure is simplified and schematic and in fact many more than 6 lipid bilayers are present.

FIG. 4 is an enlargement of the vesicle of FIG. 3 showing in more detail the central core compartment and parts of some of the lipid bilayers. The central core compartment 9 is occupied by an aqueous emulsion composed of water 10 as continuous phase and lipophilic droplets or fine solid particles 11 as dispersed phase. The lipophilic droplets or fine solid particles are surrounded by a layer of surfactant molecules 12, the hydrophilic portions 13 of each surfactant molecule extending into the aqueous phase and the hydrophobic portions being at the surface of the oil droplets.

Surrounding the core compartment is the innermost lipid bilayer 15. The lipid bilayer is composed of two layers of lipid molecules 16. Each lipid molecule 16 in a layer is oriented substantially parallel to adjacent lipid bilayers, and two layers that form a bilayer have the polar ends 17 of their molecules exposed to the aqueous phase and the non-polar ends 18 adjacent to each other. Between the innermost lipid bilayer 15 and the next innermost lipid bilayer 19 is a peripheral compartment 20 that is filled either with water or with the aqueous emulsion. As shown, surfactant surrounded lipophilic droplets or particles 11 can be present in the peripheral compartment 20.

Surrounding the peripheral compartment 20 is the next innermost lipid bilayer 19, which is in turn surrounded by a further peripheral compartment and a further lipid bilayer.

Lipophilic substances can be present in the lipid bilayer, as shown at 21. The lipophilic substance 21 is between the two molecular layers of the lipid bilayer, in the vicinity of the hydrophobic portions 18 of the lipid bilayers.

It will be appreciated that biologically active ingredients that are water-soluble can be present in the water of the aqueous emulsion in the central core compartment 9 and in the peripheral compartments 20. Biologically active ingredients that are lipophilic can be present in the dispersed phase of the emulsion in the central compartment 9 and in the peripheral compartments 20. They can also be present in the interior of the lipid bilayers as shown at 21. The biologically active ingredient can constitute the lipophilic droplets 21, or the biologically active ingredient can be dissolved in a lipophilic solvent that forms droplets 21. Thus the invention permits the topical application of biologically active ingredients that are water-soluble or water-insoluble.

In one preferred embodiment of the invention, the lipophilic substance is a consistency enhancer, as discussed further below.

Biologically active agents that can be entrapped within the multilammellar lipid vesicles include, but are not limited to, nucleic acids, polynucleotides, anti-bacterial compounds, antiviral compounds, antifungal compounds, anti-parasitic compounds, tumoricidal compounds, proteins, toxins, enzymes, hormones, neurotransmitters, glycoproteins, immunoglobulins, immunomodulators, dyes, radiolabels, radio-opaque compounds, fluorescent compounds, polysaccharides, cell receptor binding molecules, anti-inflammatories, antiglaucomic agents, mydriatic compounds, local anesthetic, nucleoside analogues, etc.

They also include, but are not restricted to, prostaglandins, local anesthetic agents, proteins and peptides, antiviral agents, vitamins, antiinflammatory agents, antifungal agents, corticosteroids, plant extracts, amino acids and nucleoside analogues. Specific examples include $PGE_1$, tetracaine, lidocaine, etidocaine, interferon alpha, interferon gamma, adenine-β-D-arabinofuranoside (Ara-A), 5-methoxymethyl-2'-deoxyuridine (MMUdR), vitamin A, vitamin C, vitamin E, provitamin $B_5$, azulene, allantoin, alpha-bisabolol and L-carnitine.

FIG. 1 is a scanned image, magnified 440× of vesicles made in accordance with product 5, "Topical liposomal product with encapsulated lipophilic drug in multicompartments with encapsulated oil droplet and consistency enhancer" described further below. This product displayed the consistency of a lotion or semi-solid cream. Inspection of the scanned image reveals multilamellar structures with uniform size distribution. These have displayed physical stability for extended periods of time of more than one year.

In order to demonstrate the difference in properties observed in the liposome population produced in accordance with the preferred method of the present invention, comparative tests were conducted between two liposome compositions prepared from the same ingredients but using in one case the solvent evaporation method and in the other case the preferred anhydrous plastic proliposome gel method. FIG. 2*a* is a scanned image of the liposome population prepared using the anhydrous proliposome gel ('melt' or 'fusion') method and FIG. 2*b* is a scanned image of the liposome population prepared using the solvent evaporation method. As can be seen, the liposome population obtained using the anhydrous plastic proliposome gel method has a liposome size distribution which is substantially more uniform than that obtained using the solvent evaporation method. Also, minimal amounts of aggregated or fused liposomes are formed when using the anhydrous plastic proliposome gel method, whereas large aggregates can be observed in the liposome population obtained using the solvent evaporation method. Table 1 summarizes the physical properties of the liposome formulations shown in FIGS. 2*a* and 2*b*.

TABLE 1

Comparison of two identical formulas prepared by:

a) solvent evaporation method (Formula #2)
b) "anhydrous plastic proliposome-gel" ('fusion') method (Formula #1)

| Product No. | Organoleptic properties | Microscopyl/liposome size distribution |
|---|---|---|
| 1 (FIG. 2a) | white cream, homogeneous | MLV, 1–10 μm, even distribution of liposomes, no fusion or aggregation |
| 2 (FIG. 2b) | white cream, homogeneous | MLV, 1–30 μm, aggregation, fusion |

Also, it has been demonstrated that the encapsulation efficiency of proteins into liposomes is higher, or at least as high, as the encapsulation efficiency using the solvent evaporation method without the drawback of traces of toxic solvents such as chloroform that are observed with the solvent evaporation method. Furthermore, it is important to mention that encapsulation seems to be more reproducible when using the anhydrous plastic proliposome gel method which presents a much smaller standard deviation than the solvent evaporation method. The results are summarized in Table 2.

TABLE 2

Encapsulation efficiency of interferon alpha into liposomes

| Product No. | Encapsulation efficiency % ± s.d. (n = 5) |
|---|---|
| 1 | 55.9 ± 1.5 |
| 2 | 59.1 ± 10.4 |

In some embodiments of the invention the lipophilic substance is an oil or solid/semisolid lipophilic consistency enhancer which can be encapsulated into liposomes. As solid or semisolid lipophilic consistency enhancers there are mentioned fatty alcohols, waxes, fatty alcohol fatty acid esters, glyceride esters, white petrolatum and mixtures thereof. Examples of oils which have successfully been encapsulated into liposomes include: olive oil, macadamia nut oil, rice bran oil, pumpkin seed oil, apricot kernel oil, hazelnut oil, rose hip seed oil, borage oil, tea tree oil, rocou oil, camellia oil, sweet almond oil, safflower oil, St. John's wort oil, lipodermol, pistachio nut oil, chia oil, kiwi seed oil, lesquerella oil, tiare oil, grapeseed oil, peanut oil, babassu oil, avocado oil, squalene, evening primrose oil, blackcurrent oil, pentaerythritol tetracaprylate/caprate, pentaerythritol tetraisostearate, cetearyl octanoate and canola oil, jojoba oil, peanut oil, rice bran oil, cottonseed oil, sunflower oil, corn oil, walnut oil, avocado oil, peru balsam, clove oil and eugenol. Plant extracts based on oil have also been successfully incorporated into liposomes such as from comfrey, German chamomile, cola nut, pot marigold, silver birch, gingko bilola, witch hazel, willow, guarana, arnica, horse chestnut, eucalyptus, meadow sweet, rosemary, phyt'Iod, coffee, mate, tea and ivy. Solid/semi solid lipophilic consistency enhancer ingredients can be selected from waxes, fatty alcohols, fatty acid esters, glyceryl stearate, petrolatum or combinations thereof. Specific examples of preferred consistency enhancers include beeswax, glyceryl tribehenate, glyceryl stearate, stearyl heptanoate, stearyl palmitate, cetyl alcohol, stearyl alcohol, myristyl myristate, behenyl erucate and cetyl palmitate.

The viscosity of a composition of vesicles in accordance with the invention and containing a consistency enhancer is greater than the viscosity of corresponding vesicles that do not include a consistency enhancer but are otherwise identical. By varying the amount of consistency enhancer it is possible to achieve virtually any required viscosity, from a relatively mobile liquid, to a "lotion", to "creamy" to "thick cream". Determination of amounts of consistency enhancer to achieve a particular viscosity of the composition can be determined by routine experiment.

The surfactant used to coat the oil droplet or the solid/semisolid lipophilic consistency enhancer ingredients is important for the successful encapsulation of a lipophilic core into multilamellar lipid vesicles. About 30 different types of surfactants were screened and primary cationic emulsifiers were found to give the most acceptable results. The most preferred surfactant is linoleamidopropyl PG-Dimonium chloride phosphate, a synthetic phospholipid complex. This surfactant is commercially available from Mona Industries Inc., Patterson N.J. under the trade name PHOSPHOLIPID EFA, abbreviated herein PEFA. Two other members of this family, also from Mona Industries, are stearamidopropyl PG-dimonium chloride phosphate, trade name PHOSPHOLIPID SV, and cocamidopropyl PG-dimonium chloride phosphate, trade name PHOSPHOLIPID PTC, are also acceptable but PEFA is preferred. Nonionic or amphoteric surfactants can also be used, such as naturally derived emulsifiers: PEG-60 almond glycerides, avocado oil diethanolamine, ethoxylated jojoba oil (PEG-40 Jojoba acid and PEG-40 Jojoba alcohol); polyoxyethylene derivatives: polyoxyethylene (20) sorbitan monooleate, polyoxyethylene (20) sorbitan monostearate; lanolin derivatives: polychol 20 (Laneth 20), polychol 40 (laneth 40); neutral phosphate esters: PPG-cetyl ether phosphate, DEA oleth-3 phosphate. It is also possible to use anionic surfactants such as acylglutamates: TEA-cocoyl glutamate, sodium lauroyl glutamate, sodium hydrogenated tallow glutamate and sodium cocoyl glutamate.

The required HLB number of the surfactant used to emulsify the oil phase depends upon the particular lipophile to be emulsified, but it is usually above about 6. The following table gives some typical values.

| Component to be emulsified in O/W emulsion | Required HLB |
|---|---|
| Cetyl alcohol | 13 |
| Mineral oil, light | 10–12 |
| Beeswax | 10–16 |
| Vegetable oils | 6–10 |

For an oil phase that is composed of two or more components the required HLB is calculated from the required HLB of the individual components. For example, with a three-component system:

| | Required HLB | Fraction of the oil phase | Proportional HLB requirement for each component |
|---|---|---|---|
| Component 1 (15 g) | 13 | 15/45 | 15/45 × 13 = 4.33 |
| Component 2 (25 g) | 10 | 25/45 | 25/45 × 10 = 5.55 |
| Component 3 (5 g) | 9 | 5/45 | 5/45 × 9 = 1 |
| Final required HLB (sum of components) | | | 10.88 |

It is desirable that the surfactant has a high critical micellar concentration (CMC).

When preparing the lipophilic substance-in-water emulsion, the hydrophilic ingredients and surfactants are all incorporated in water. Once the water phase of the emulsion has been prepared, the oil and/or solid/semisolid lipophilic ingredients are added to the water in a homogenizer for a period of time ranging from 5 to 30 minutes to obtain relatively small droplet size. Preferred droplet size ranges from 0.1 $\mu$m to 1 $\mu$m, most preferably below about 0.5 $\mu$m. The lipid phase melt is then heated and the lipophilic substance-in-water emulsion is added and vigorously mixed by either vortexing or propeller mixing depending on the product size.

The formulation procedure described above can be easily adopted for large scale manufacturing. The propeller mixing approach can be directly scaled up by geometrically increasing the size of the vessel and the diameter of the propeller mixer. However, as the vessel size increases, a preferred set up might be a combination mixer such as a high intensity mixer with propeller mixer and a scraped surface agitator. In a large scale operation, the lipophilic substance-in-water emulsion can be pumped from a first tank into a second tank containing the anhydrous plastic proliposome gel at the required temperature and mixed.

With the multilamellar lipid vesicle of the present invention, oil droplets containing solubilized lipophilic biologically active compounds or oily plant extracts can be delivered through liposome encapsulation. Furthermore, the possibility of multicompartment encapsulation provides drug release over extended periods of time. Also, encapsulation of lipophilic solid/semisolid consistency enhancers into the central lipophilic core compartment provides enhanced viscosity to the final liposome composition. In this case, the addition of viscosity-increasing agents in the final liposome preparation can be avoided.

Overall, the preparation of multilamellar lipid vesicles with a central emulsion core component provides a physically stable, uniform liposome composition. The composition has a viscosity that is suitable for topical administration and can be easily manufactured on a large scale.

DESCRIPTION WITH REFERENCE TO THE EXAMPLES

There are provided below examples of various ingredients that have been made into biphasic multilamellar lipid vesicles by the preferred method using the anhydrous proliposome gel. All were prepared by the following procedure.

Encapsulation of lipophilic solid or liquid active ingredient or consistency enhancer into the central core compartment of multilamellar lipid vesicles The lipid ingredients and the hydrophilic solvent, propylene glycol, were weighed into a glass vial or beaker and melted at 65–75° C. by intermittent heating on a hot water bath, to form the anhydrous proliposome gel.

The hydrophilic ingredients and the oil droplets or solid/semisolid lipophilic ingredients were prepared separately as an oil in water (o/w) emulsion. The emulsion was prepared by dissolving the surfactant in distilled water and adding the oil and/or solid/semisolid lipophilic ingredients to the water at 60–80° C. in a homogenizer at 20–80 psig for 5–30 minutes to obtain small droplet size (<about 0.5 $\mu$m).

The proliposome gel was heated to 55° C., the emulsion was added and the gel and emulsion were vigorously mixed by vortexing or propeller mixing depending on the product size.

$PGE_1$ was stored as an ethanolic solution at −20° C. Prior to its incorporation in a liposomal formulation the ethanol was evaporated under nitrogen and the proliposome gel was added to the solid $PGE_1$ and mixed thoroughly by intermittent warming and vortex agitation.

A. COMPOSITIONS FREE OF BIOLOGICALLY ACTIVE MATERIAL BUT SUITABLE FOR USE AS A VEHICLE FOR ADMINISTRATION OF SUCH A MATERIAL

1. Topical liposomal product with encapsulated oil droplet

| | % (w/w) |
|---|---|
| Proliposome gel: | |
| Phospholipon 90H | 5.0 |
| Cholesterol | 2.0 |
| Stearic acid | 1.0 |
| Propylene glycol | 7.0 |
| Emulsion: | |

-continued

| | % (w/w) |
|---|---|
| Part 1: Distilled water | q.s. to 100 |
| PEFA | 4.0 |
| Methylparaben | 0.15 |
| Propylparaben | 0.05 |
| Part 2: Olive oil | 10.0 |

2. Topical liposomal product with encapsulated consistency enhancer

| | % (w/w) |
|---|---|
| Proliposome gel: | |
| Phospholipon 90H | 5.0 |
| Cholesterol | 2.0 |
| Stearic acid | 1.0 |
| Propylene glycol | 7.0 |
| Emulsion: | |
| Part 1: Distilled water | q.s. to 100 |
| PEFA | 4.0 |
| Methylparaben | 0.15 |
| Propylparaben | 0.05 |
| Part 2: Glyceryl stearate | 1.0 |
| Cetyl alcohol | 0.6 |
| Synthetic beeswax | 0.28 |

3. Topical liposomal product with encapsulated oil droplet and consistency enhancer

| | % (w/w) |
|---|---|
| Proliposome gel: | |
| Phospholipon 90H | 5.0 |
| Cholesterol | 2.0 |
| Stearic acid | 1.0 |
| Propylene glycol | 7.0 |
| Emulsion: | |
| Part 1: Distilled water | q.s. to 100 |
| PEFA | 4.0 |
| Methylparaben | 0.15 |
| Propylparaben | 0.05 |
| Part 2: Olive oil | 10.0 |
| Glyceryl stearate | 1.0 |
| Cetyl alcohol | 0.6 |
| Synthetic beeswax | 0.28 |

B. COMPOSITIONS CONTAINING $PGE_1$

4. Topical liposomal prostaglandin $E_1$

| | % (w/w) |
|---|---|
| Proliposome gel: | |
| Phospholipon 90H | 15.0 |
| Cholesterol | 1.5 |
| Ascorbyl Palmitate | 0.05 |
| Monolauroyllysine | 1.0 |
| Stearic Acid | 0.5 |
| Centrolex P | 0.3 |
| Methyl salicylate | 2.0 |
| Prostaglandin $E_1$ | 0.05 |
| Propylene glycol | 7.0 |
| Aqueous Phase | q.s. to 100 |
| Sodium chloride | 0.9 |
| Triethanolamine | 0.5 |
| Glycerol | 5.0 |

-continued

| | % (w/w) |
|---|---|
| Methylparaben | 0.1 |
| Propylparaben | 0.02 |
| Distilled water | 98.48 |

5. Topical liposomal product with encapsulated lipophilic drug in multicompartments and with encapsulated oil droplet and consistency enhancer

| | % (w/w) |
|---|---|
| Proliposome gel: | |
| Phospholipon 90H | 5.0 |
| Cholesterol | 2.0 |
| Stearic acid | 1.0 |
| Propylene glycol | 7.0 |
| Prostaglandin $E_1$ | 0.05 |
| Propylene glycol | 7.0 |
| Emulsion: | |
| Part 1: Distilled water | q.s. to 100 |
| PEFA | 4.0 |
| Methylparaben | 0.15 |
| Propylparaben | 0.05 |
| Part 2: Olive oil | 10.0 |
| Glyceryl stearate | 1.0 |
| Cetyl alcohol | 0.6 |
| Synthetic beeswax | 0.28 |
| Prostaglandin $E_1$ | 0.05 |

6. Topical liposomal product with encapsulated $PGE_1$ oil and consistency enhancer

| | % (w/w) |
|---|---|
| Proliposome gel: | |
| Phospholipon 90H | 5.0 |
| Cholesterol | 1.5 |
| Monolauroyllysine | 1.0 |
| Stearic acid | 0.5 |
| Prostaglandin $E_1$ | 0.5 |
| Propylene glycol | 7.0 |
| Emulsion: | |
| Part 1: Distilled water | q.s. to 100 |
| PEFA | 4.0 |
| Methylsalicylate | 2.0 |
| α-tocopherylnicotinate | 1.0 |
| Methylparaben | 0.15 |
| Propylparaben | 0.05 |
| Part 2: Macadamia nut oil | 3.0 |
| Glyceryl stearate | 1.0 |
| Cetyl alcohol | 0.6 |
| Synthetic beeswax | 0.28 |

7. Topical liposomal product with $PGE_1$

| | % (w/w) |
|---|---|
| Proliposome Gel: | |
| Phospholipon 90H | 15% |
| Cholesterol | 2% |
| Ascorbyl Palmitate | 0.05% |
| Phospholipon 80 | 1% |
| Prostaglandin $E_1$ | 0.05% |
| Propylene Glycol | 7% |
| Aqueous Phase F | q.s. to 100 |
| NaCl | 0.9% |

-continued

| | % (w/w) |
|---|---|
| Ethanol | 10% |
| dd, $H_2O$ | 89.1% |
| pH | 5.5 |
| Encapsulation Efficiency: | 16% |

8. Topical liposomal product with $PGE_1$

| | % (w/w) |
|---|---|
| Proliposome Gel: | |
| Phospholipon 90H | 15% |
| Cholesterol | 1.5% |
| Ascorbyl Palmitate | 0.05% |
| Propylene glycol | 7% |
| Monolauroyllysine | 1% |
| Glycerol | 5% |
| Stearic Acid | 0.5% |
| Centrolex P | 0.3% |
| Prostaglandin $E_1$ | 0.05% |
| Aqueous Phase 16 | q.s. to 100 |
| NaCl | 0.9% |
| Methylparaben | 0.1% |
| Propylparaben | 0.02% |
| Triethanolamine | 0.5% |
| dd, $H_2O$ | 98.48% |
| pH | 8.3 |
| Encapsulation Efficiency: | 81% |

9. Topical liposomal product with $PGE_1$

| | % (w/w) |
|---|---|
| Proliposome Gel: | |
| Phospholipon 90H | 15% |
| Cholesterol | 1.5% |
| Ascorbyl Palmitate | 0.05% |
| Monolauroyllysine | 1% |
| Glycerol | 5% |
| Lauric Acid | 0.5% |
| Centrolex P | 0.3% |
| Prostaglandin $E_1$ | 0.05% |
| Aqueous Phase 16 (see above) | q.s. to 100 |
| Encapsulation Efficiency: | 76% |

10. Topical liposomal product with $PGE_1$

| | % (w/w) |
|---|---|
| Proliposome Gel: | |
| Phospholipon 90H | 15% |
| Cholesterol | 1.5% |
| Ascorbyl Palmitate | 0.05% |
| Propylene glycol | 7% |
| Monolauroyllysine | 1% |
| Glycerol | 5% |
| Oleic Acid | 1% |
| Centrolex P | 0.3% |
| Prostaglandin $E_1$ | 0.05% |
| Aqueous Phase 16 (see above) | q.s. to 100 |
| Encapsulation Efficiency: | 67% |

11. Topical liposomal product with $PGE_1$

| | % (w/w) |
|---|---|
| Proliposome Gel: | |
| Phospholipon 90H | 15% |
| Cholesterol | 1.5% |
| Ascorbyl Palmitate | 0.05% |
| Propylene glycol | 7% |
| Monolauroyllysine | 1% |
| Glycerol | 5% |
| Stearic Acid | 0.5% |
| Centrolex P | 0.3% |
| Methylsalicylate | 2% |
| Prostaglandin $E_1$ | 0.05% |
| Aqueous Phase 16 (see above) | q.s. to 100 |
| Encapsulation Efficiency: | 33% |

12. –0.1% Topical liposomal product with $PGE_1$

| | % (w/w) |
|---|---|
| Proliposome Gel: | |
| Phospholipon 90H | 15% |
| Cholesterol | 1.5% |
| Ascorbyl Palmitate | 0.05% |
| Propylene glycol | 7% |
| Monolauroyllysine | 1% |
| Glycerol | 5% |
| Stearic Acid | 0.5% |
| Centrolex P | 0.3% |
| Methylsalicylate | 2% |
| Prostaglandin $E_1$ | 0.1% |
| Aqueous Phase 16 (see above) | q.s. to 100 |

13. Topical liposomal product with $PGE_1$

| | % (w/w) |
|---|---|
| Proliposome Gel: | |
| Phospholipon 90H | 15% |
| Cholesterol | 1.5% |
| Ascorbyl palmitate | 0.05% |
| Propylene glycol | 7.0% |
| Monolauroyllysine | 1.0% |
| Glycerol | 5.0% |
| Stearic acid | 0.5% |
| Centrolex P | 0.3% |
| Prostaglandin $E_1$ | 0.05% |
| Calcium thioglycolate | 1.0% |
| Aqueous phase 16 (see above) | q.s. to 100% |

Of the $PGE_1$-containing products, products Nos. 4, 7, 8, 9, 10, 11, 12 and 13 were prepared with an aqueous solution rather than an emulsion. As is demonstrated in products Nos. 5 and 6, however, by incorporating a lipophilic consistency enhancer and a surfactant it is possible to prepare vesicles that have an emulsion in the central core compartment and which display enhanced consistency, rendering them particularly suitable in compositions for topical application.

C. COMPOSITION CONTAINING LOCAL ANAESTHETIC

14. Topical liposomal product with encapsulated lipophilic drug in multicompartments and with encapsulated oil droplet and consistency enhancer

| | % (w/w) |
|---|---|
| Proliposome Gel: | |
| Phospholipon 90H | 5.0 |
| Cholesterol | 2.0 |
| Stearic acid | 1.0 |
| Tetracaine | 1.0 |
| Propylene glycol | 7.0 |
| Emulsion: | |
| Part 1: Distilled water | q.s. to 100 |
| PEFA | 4.0 |
| Methylparaben | 0.15 |
| Propylparaben | 0.05 |
| Part 2: Olive oil | 10.0 |
| Glyceryl stearate | 1.0 |
| Cetyl alcohol | 0.6 |
| Synthetic beeswax | 0.28 |
| Tetracaine | 1.0 |

D. COMPOSITION CONTAINING AN ANTI-VIRAL AGENT

15. Topical liposomal product with encapsulated antiviral drug combination with or without consistency enhancer

| | % (w/w) |
|---|---|
| Proliposome gel: | |
| Phospholipon 90H | 10.0 |
| Phospholipon 90 | 0.5 |
| Cholesterol | 1.0 |
| Stearic acid | 1.0 |
| Propylene glycol | 7.0 |
| Ara-A | 1.0 |
| MMUdR | 1.0 |
| Aqueous phase F | q.s. to 100 |
| OR: | |
| Emulsion: | |
| Part 1: Distilled water | q.s. to 100 |
| PEFA | 4.0 |
| Methylparaben | 0.15 |
| Propylparaben | 0.05 |
| Part 2: Canola oil | 10.0 |

E. COMPOSITIONS CONTAINING A PROTEIN (INTERFERON ALPHA and INTERFERON GAMMA)

16. Topical liposomal product with encapsulated protein drug and with encapsulated oil droplet and consistency enhancer

| | % (w/w) |
|---|---|
| Proliposome Gel: | |
| Phospholipon 90H | 5.0 |
| Cholesterol | 2.0 |
| Monolauroyllysine | 2.0 |
| Propylene glycol | 7.0 |
| Emulsion: | |
| Part 1: Phosphate buffer | q.s. to 100 |
| PEFA | 4.0 |
| Methylparaben | 0.15 |
| Propylparaben | 0.05 |
| Interferon alpha | 20 MU |
| Part 2: Olive oil | 10.0 |
| Glyceryl stearate | 1.0 |
| Cetyl alcohol | 0.6 |
| Synthetic beeswax | 0.28 |

17. Topical liposomal product with encapsulated protein drug and consistency enhancer

| | % (w/w) |
|---|---|
| Proliposome Gel: | |
| Phospholipon 90H | 5.0 |
| Cholesterol | 2.0 |
| Monolauroyllysine | 2.0 |
| Propylene glycol | 7.0 |
| Emulsion: | |
| Part 1: Phosphate buffer | q.s. to 100 |
| PEFA | 4.0 |
| Methylparaben | 0.15 |
| Propylparaben | 0.05 |
| Interferon gamma | 2 MU |
| Part 2: Glyceryl stearate | 1.0 |
| Cetyl alcohol | 0.6 |

F. COMPOSITIONS CONTAINING HERBAL EXTRACTS

18. Topical liposomal product with encapsulated oily plant extract and consistency enhancer

| | % (w/w) |
|---|---|
| Proliposome Gel: | |
| Phospholipon 90H | 5.0 |
| Cholesterol | 2.0 |
| Stearic acid | 1.0 |
| Propylene glycol | 7.0 |
| Emulsion: | |
| Part 1: Distilled water | q.s. to 100 |
| PEFA | 4.0 |
| Methylparaben | 0.15 |
| Propylparaben | 0.05 |
| Part 2: German chamomile oily extract | 5.0 |
| Glyceryl stearate | 1.0 |
| Cetyl alcohol | 0.6 |
| Synthetic beeswax | 0.28 |

19. Topical liposomal product with encapsulated oil and oil-soluble cosmetic active ingredient and consistency enhancer

| | % (w/w) |
|---|---|
| Proliposome gel: | |
| Phospholipon 90H | 5.0 |
| Cholesterol | 2.0 |
| Propylene glycol | 7.0 |
| Emulsion: | |
| Part 1: Distilled water | q.s. to 100 |
| PEFA | 4.0 |
| Methylparaben | 0.15 |
| Propylparaben | 0.05 |
| Part 2: Azulenol | 0.1 |
| Rose hip seed oil | 5.0 |
| Glyceryl stearate | 1.0 |
| Cetyl alcohol | 0.6 |
| Synthetic beeswax | 0.28 |

20. Topical liposomal product with encapsulated oil and oil-soluble cosmetic active ingredient and consistency enhancer

| | % (w/w) |
|---|---|
| Proliposome Gel: | |
| Phospholipon 90H | 5.0 |
| Cholesterol | 2.0 |
| Propylene glycol | 7.0 |
| Emulsion: | |
| Part 1: Distilled water | q.s. to 100 |
| PEFA | 4.0 |
| Methylparaben | 0.15 |
| Propylparaben | 0.05 |
| Part 2: Alpha bisabolol | 10.0 |
| Rocou ami oil | 3.0 |
| Glyceryl stearate | 1.0 |
| Cetyl alcohol | 0.6 |
| Synthetic beeswax | 0.28 |

G. COMPOSITIONS CONTAINING VITAMINS

21. Topical liposomal product with encapsulated oil-soluble cosmetic active ingredient and consistency enhancer

| | % (w/w) |
|---|---|
| Proliposome Gel: | |
| Phospholipon 90H | 5.0 |
| Cholesterol | 2.0 |
| Stearic acid | 1.0 |
| Propylene glycol | 7.0 |
| Emulsion: | |
| Part 1: Distilled water | q.s. to 100 |
| PEFA | 4.0 |
| Methylparaben | 0.15 |
| Propylparaben | 0.05 |
| Part 2: Vitamin E | 10.0 |
| Glyceryl stearate | 1.0 |
| Cetyl alcohol | 0.6 |
| Synthetic beeswax | 0.28 |

22. Topical liposomal product with encapsulated oil-soluble cosmetic active ingredients (vitamins) and consistency enhancer

| | % (w/w) |
|---|---|
| Proliposome Gel: | |
| Phospholipon 90H | 5.0 |
| Cholesterol | 2.0 |
| Stearic acid | 1.0 |
| Ascorbyl palmitate | 0.5 |
| Propylene glycol | 7.0 |
| Emulsion: | |
| Part 1: Distilled water | q.s. to 100 |
| PEFA | 4.0 |
| Methylparaben | 0.15 |
| Propylparaben | 0.05 |
| Part 2: Vitamin E | 10.0 |
| Vitamin A | 2.0 |
| Glyceryl stearate | 1.0 |
| Cetyl alcohol | 0.6 |
| Synthetic beeswax | 0.28 |

Encapsulation of prostaglandins and prostaglandin analogs into multilamellar lipid vesicles Liposome encapsulated prostaglandins and prostaglandin analogs can provide benefit in a number of treatment areas. The following table summarizes the utility of liposome encapsulated prostaglandins. The advantage of liposomal delivery of these prostaglandins is the more efficient, localized and targeted delivery to the desired tissues i.e. the skin, mucus membranes and surrounding tissues. The liposome system can be designed to provide a slow release depot at the target site within the skin or mucus membrane or localize the drug in the eye through bioadhesion and slow release or promote transdermal flux of the encapsulated drug.

| Prostaglandin | Effect and use |
|---|---|
| PGE1 | Vasodilatation: peripheral vascular diseases, ischaemic leg ulcers, wound healing, various skin conditions such as psoriasis, atopic dermatitis |
| PGE2 | cervical ripening or labour induction by local administration into the cervical canal or intravaginally; vasodilatation: peripheral vascular diseases |
| PGA and J series | anticancer and antiviral agents |
| PGF and derivatives | ocular hypotensive: glaucoma |

Encapsulation of $PGE_1$ into multilamellar lipid vesicles for the preparation of liposome composition used in the treatment of erectile dysfunctions In order to overcome the problems associated with the administration of $PGE_1$ by injection, the present invention provides a new dosage form which can be applied topically. $PGE_1$ is incorporated into liposomes which permit penetration of $PGE_1$ through the skin of a penis to deliver a clinically useful concentration of drug into the corpus cavernosum. Liposome encapsulation enhances the penetration of the encapsulated $PGE_1$ through the penile skin and at the same time protects the drug within the skin from premature metabolism before reaching the target site. These properties make liposomes a suitable delivery system for $PGE_1$ in the treatment of impotence.

$PGE_1$ is a lipid-soluble drug. Therefore, it can be encapsulated in the lipid bilayers and/or the central lipophilic core of the liposomes. The encapsulation efficiency of $PGE_1$ into liposomes is manipulated by varying lipid composition, lipid/drug ratio, pH and the concentration of other excipients. Specific liposome compatible penetration enhancers/release agents are employed in designing an optimal liposomal $PGE_1$ preparation for dermal or transdermal delivery.

The compositions of selected liposomal $PGE_1$ formulations developed for transdermal delivery (Products 5, 6, 7, 8, 11 and 12—0.1%) and for dermal delivery (Products 9 and 10) are given above. The liposomal formulations for the transdermal delivery of $PGE_1$ contain saturated and/or unsaturated phospholipids, especially phosphatidylcholine, lysophosphatidylcholine, phosphatidylserine, phosphatidylethanolamine, glycolipids. The liposomes also contain cholesterol, saturated long chain fatty acids (e.g. stearic acid) to improve physical stability and appearance of the product. The phospholipids are in combination with a penetration enhancing agent such as monolauroyllysine and/or methyl salicylate to achieve predominantly transdermal delivery potential.

The liposomal formulations for the dermal delivery of $PGE_1$ can contain saturated and/or unsaturated phospholipids, especially phosphatidylcholine, lysophosphatidylcholine, phosphatidylserine, phosphatidylethanolamine, glycolipids and ceramides. The liposomes may also contain cholesterol. To achieve predominantly dermal delivery cutaneous release agents such as unsaturated fatty acids (oleic acid) or short chain fatty acids (lauric acid) is added.

In vitro testing of percutaneous absorption of $PGE_1$

The rate of diffusion of $PGE_1$ from the liposome preparations across full thickness adult foreskin from circumcision surgery was investigated using Teflon® Flow-Thru Diffusion Cells (Crown Glass Co. Inc. Somerville, N.J.) which have a surface area for diffusion of 0.32 $cm^2$. The diffusion cells are designed such that fluid may be continuously pumped through them in order to maintain sink conditions. A phosphate buffer (7.5 mM $Na_2HPO_4$, 141.2 mM NaCl) isotonic with body fluids and having a pH of 7.2 was used as the perfusion fluid.

The diffusion cells were mounted in a PosiBloc™ Diffusion Cell Heater (Crown Glass Co. Inc., Somerville, N.J.) maintained at 32° C. by a circulating water bath. The flow rate was 3 mL per hour. Each experiment was conducted for a period of 24 hours continuously. Liposome preparation (20 mg) containing 10 μg $PGE_1$ and $^3$H-prostaglandin $E_1$ as tracer, was applied to each cell at the beginning of each experiment. This amount is estimated to be roughly equivalent to the dose per unit surface area of the preparation (1.5 g) that was applied on the shaft of the penis in the clinical trials. At least three replicates of each experiment were performed. The quantity of $PGE_1$ in each fraction was determined by liquid scintillation counting.

Skin penetration parameters were calculated from the steady state part of the cumulative flux plots as follows:

a) Permeability Coefficient, P=J/ΔC where J=steady state slope and ΔC=concentration of $PGE_1$ in the donor chamber b) Diffusion Coefficient, D=$h^2$/6L where h=mean thickness of foreskin specimen=1 mm and L=lag time in seconds.

For the treatment of impotence there is a requirement to deliver 5–40 μg $PGE_1$ (the equivalent amount delivered during intracavernous injection) transdermally. This amount should be delivered within short period (ideally within 1 h) to be practically useful. The data obtained shows that $PGE_1$ can be delivered transdermally by appropriate liposomal formulas.

Table 4 shows the percutaneously delivered $PGE_1$ in vitro through human foreskin. Products 6, 7, 8, 11 and 12—0.1% illustrate the formulation approach to develop a transdermal product.

TABLE 4

Percutaneous absorption of $PGE_1$ from liposomal formulations in 24 hours

| Product # | μg/cm² ± S.D. | % of Total applied ± S.D. |
|---|---|---|
| 6 | 24.95 ± 8.35 | 6.25 ± 2.09 (n = 8) |
| 7 | 0.96 ± 0.87 | 2.14 ± 1.95 (n = 3) |
| 8 | 1.39 ± 1.56 | 3.87 ± 4.34 (n = 8) |
| 11 | 3.51 ± 2.80 | 9.93 ± 7.93 (n = 6) |
| 12-0.1% | 6.73 ± 3.97 | 8.74 ± 5.15 (n = 6) |
| 9 | 0.06 ± 0.04 | 0.17 ± 0.12 (n = 3) |
| 10 | 0.34 ± 0.55 | 0.89 ± 1.43 (n = 3) |
| Non-liposomal* | 0.38 ± 0.61 | 1.03 ± 1.64 (n = 3) |

*CONVENTIONAL (NON-LIPOSOMAL) PRODUCT
Prostaglandin $E_1$ 0.05%
Dermabase q.s.

The initial drug concentration used in these formulas was 0.05%. Effective drug concentration in these formulas can vary between 0.01–5%. As illustrated with products 11 and 12—0.1%, increasing drug concentration to 0.1% doubled the amount of transdermally delivered $PGE_1$.

The percutaneous absorption parameters are shown in Table 5. The flux values obtained for the products correlated well with their in vivo efficacy assessed by doppler ultrasonography. The higher flux values indicate higher potency in the patients. Products 9 and 10 show low transdermal delivery potential.

TABLE 5

In vitro skin penetration parameters

| PRODUCT # | LAG TIME [h] | STEADY STATE FLUX (J) [μg/cm²/h] | DIFFUSION COEFFICIENT (D) [cm²/s × $10^{-8}$] | PERMEABILITY COEFFICIENT (P) [cm/h × $10^4$] |
|---|---|---|---|---|
| 6 | 9.6 | 1.664 | 4.80 | 3.33 |
| 7 | 8.5 | 0.059 | 5.50 | 1.18 |
| 8 | 7.9 | 0.083 | 5.86 | 1.66 |
| 11 | 7.7 | 0.191 | 6.01 | 3.82 |
| 12-0.1% | 9.5 | 0.427 | 4.87 | 4.27 |
| 9 | 10.6 | 0.004 | 4.37 | 0.02 |
| 10 | 12.8 | 0.029 | 3.62 | 0.58 |
| Nonliposomal | 15.1 | 0.042 | 3.07 | 0.84 |

Table 6 shows the extent of delivery of $PGE_1$ with the various products. Products 9 and 10 are examples for achieving predominantly cutaneous delivery.

TABLE 6

Cutaneous delivery of $PGE_1$ from liposomal formulations

| Product # | Whole skin μg/cm² | Whole skin %* | Stratum corneum μg/cm² | Stratum corneum %* | Viable epidermis + dermis μg/cm² | Viable epidermis + dermis %* |
|---|---|---|---|---|---|---|
| 6 (n = 8) | 44.50 ± 15.10 | 11.47 ± 4.85 | 14.01 ± 6.48 | 3.62 ± 1.96 | 39.29 ± 24.33 | 9.60 ± 5.15 |
| 7 (n = 3) | 7.11 ± 2.63 | 15.98 ± 3.87 | 0.85 ± 0.84 | 1.84 ± 1.63 | 6.99 ± 3.39 | 14.80 ± 4.07 |
| 8 (n = 8) | 4.15 ± 2.79 | 11.97 ± 7.99 | 0.23 ± 0.15 | 0.74 ± 0.48 | 3.83 ± 2.72 | 11.16 ± 8.57 |
| 11 (n = 6) | 4.96 ± 2.15 | 14.18 ± 6.32 | 0.32 ± 0.20 | 0.93 ± 0.66 | 4.27 ± 3.21 | 12.11 ± 8.88 |
| 12-01 (n = 6) | 20.25 ± 7.44 | 26.16 ± 8.30 | 0.54 ± 0.23 | 0.71 ± 0.28 | 15.54 ± 8.56 | 20.46 ± 8.21 |
| 9 (n = 3) | 1.71 ± 0.83 | 4.85 ± 1.73 | 0.17 ± 0.08 | 0.50 ± 0.27 | 0.89 ± 0.78 | 0.251 ± 2.13 |
| 10 (n = 3) | 5.82 ± 4.21 | 14.89 ± 10.18 | 0.14 ± 0.06 | 0.37 ± 0.15 | 4.70 ± 4.43 | 11.80 ± 10.33 |

*% of total applied

The transdermal versus dermal delivery potential of these formulations is reflected in the T/D ratio (Table 7) calculated from the mean (μg) transdermally absorbed drug and the mean (μg) cutaneously (whole skin count) delivered $PGE_1$ amount.

TABLE 7

Transdermal versus dermal delivery ratios for liposomal $PGE_1$ products

| Product # | Transdermal/Dermal delivery ratios |
|---|---|
| 6 | 0.561 |
| 7 | 0.135 |
| 8 | 0.335 |
| 11 | 0.708 |
| 12-0.1% | 0.332 |
| 9 | 0.035 |
| 10 | 0.060 |

4. Physical stability of liposomal products

Physical stability of the liposomal formulations was assessed by visual and microscopic evaluation immediately after preparation and at weekly intervals following storage at room temperature, or at 4° C.

The liposomal formulas were physically stable even after prolonged storage at room temperature and at 4° C. The formulations were completely homogenous with no signs of phase separation macroscopically. Under the light microscope, numerous multilamellar liposomes of varying sizes and mostly spherical shape were seen. There was no increase in fusion or aggregation products (indicators of liposome instability) upon storage.

Stability of $PGE_1$ in liposomal formulations

Stability of $PGE_1$ was analyzed by thin-layer chromatographic (TLC) and radiometric methods.

TLC Assay

Degradation of $PGE_1$ was assessed by TLC analysis of the diffusion cell fractions and the liposomal $PGE_1$ formulation (after storage at 4° C. for 2 weeks). The aqueous fractions from diffusion cell experiments were pooled and freeze-dried. The $PGE_1$ was extracted with methanol, filtered through a Millipore filter and concentrated prior to spotting. The liposomal $PGE_1$ formulation was diluted with either methanol or dioxane prior to spotting. The mobile phase used was Benzene:Dioxane:Acetic acid (20:20:1v/v) while color reagent was Absolute Ethanol: 4-Methoxybenzaldehyde:Concentrated Sulphuric Acid (20:20:2v/v). After the chromatographic run the plate was allowed to dry, sprayed with the color reagent, allowed to dry again for at least 15 minutes and heated in the oven at 85° C. for 10 minutes for full color development. The $PGE_1$ spots appeared as dark brown spots, identical to a co-chromatographed $PGE_1$ standard.

Radiometric assay

Semi-quantitative assay of the thin-layer chromatograms was done by liquid scintillation counting of the $PGE_1$ spots and the rest of the chromatogram and expressing $PGE_1$ concentration as a percentage of total counts obtained in the chromatogram.

$PGE_1$ was positively identified on thin-layer chromatograms of the liposomal $PGE_1$ formulation after storage for 2 weeks in the refrigerator. Based on visual examination of the intensity of color development and band width, little or no $PGE_1$ degradation appeared to have occurred.

Encapsulation efficiency and leakage studies

Liposome encapsulation of $PGE_1$ is proposed to enhance its stability hence the greater the encapsulation efficiency, the more stable the drug will be in the formulation.

The encapsulation efficiency of $PGE_1$ into liposomes was determined by liquid scintillation counting. Aliquots of the liposomal cream were diluted with the aqueous phase and centrifuged at 200,000 xg for 60 minutes. The supernatant was separated from the pellet (liposomes) and the weights recorded. Calculated amounts of the supernatant and pellet were dissolved in scintillation cocktail and counted. The concentration of $PGE_1$ in each fraction were derived from the total activity (dpm) in each fraction.

Encapsulation Efficiency=Concentration of $PGE_1$ in pellet/ (Concentration in pellet and supernatant)

Encapsulation efficiency studies were repeated at weekly intervals for 2 weeks to determine leakage of encapsulated drug from liposomal formulations stored either in the refrigerator or at room temperature.

Clinical evaluations

The protocols for the human studies were accepted by the Ethics Committee on Human Experimentation at the University of Saskatchewan.

Patients included in these studies were diagnosed as having impotence of primarily organic origin. This group of patients is the most difficult to treat and they usually require higher doses of $PGE_1$. The rationale for using this "difficult" group is to decrease the possibility to obtain placebo responses.

Double blind crossover trial

Six patients diagnosed as having impotence of predominantly organic etiology and shown to respond to intracavernous $PGE_1$ injection were enrolled in the study after proper consent.

A double blind, randomized, crossover design was employed to test a liposomal $PGE_1$ against a liposomal placebo, 1.5 g of each cream was applied to the shaft of the penis at weekly intervals. Prior to this, a small amount was applied to a non-hairy part of the arm to test for adverse reactions. If none occurred within 60 minutes, the patient then proceeded with the actual test later in the day. The cream was washed off after 1 hour and prior to intercourse, if an erection was obtained. The patient was requested to note the onset, duration and quality of response as well as any side effect on the response sheets provided.

The study indicated that 5 out of 6 patients responded to the test preparation to various degrees (Response ranking ≧1, Table 8). Three patients responded with high scores (response ranking ≧2). Response to the placebo was practically zero.

TABLE 8

Pilot clinical study using product 12 (0.1%) in patients with organic impotence

| Patient # | Response ranking: Liposomal $PGE_1$ | Response ranking: Placebo |
|---|---|---|
| 1 | 3 | 0 |
| 2 | 3 | 0 |
| 3 | 2 | 0 |
| 4 | 1 | 0 |
| 5 | 1 | 1 |
| 6 | 0 | 0 |

Response ranking
0 No effect whatsoever observed.
1 Slight effect i.e. slight enlargement of the penis. No erection.
2 Erection obtained but not sufficient for intercourse.
3 Good erection obtained. Intercourse attempted but not satisfactory.
4 Good erection obtained. Satisfactory intercourse.

6.2 Doppler ultrasonography study

Doppler ultrasonography was used to assess the degree of arterial dilatation and measure penile arterial blood flow following application of transdermal liposomal $PGE_1$. Three liposomal $PGE_1$ preparations and a placebo control were tested. Test preparations were administered at no less than 2 week intervals. After initial sonographic examination to determine blood flow in the flaccid penis, the test preparation was applied on the shaft and glans penis after which an occlusive wrapping was placed around the penis. The penile blood flow was monitored at 15 minute intervals for 1 hour.

The doppler ultrasonography study on patients with predominantly organic impotence showed increased penile blood flow after topical liposomal $PGE_1$ application (Table 9), Liposome product 11 showed the greatest efficacy, with a peak flow of 32 cm/s in Patient #4. The control liposome 11 formulation (without $PEG_1$) also exhibited an increase in penile blood flow. The 11 liposome preparation is equivalent to product 8 plus a penetration enhancing agent, methyl salicylate. It is likely that this penetration enhancer increases penile blood flow to a small degree by itself and is synergistic with liposomal $PGE_1$. The in vitro percutaneous absorption data correlated very well with the doppler results. In vitro product 11 liposomal $PGE_1$ gave the highest percutaneous flux followed by product 8 and lastly, the product 13 liposomal $PGE_1$ formulation.

Product 6 was developed after the clinical and doppler tests for which results are given here. Product 6 was found to be superior to the products for which results are given.

TABLE 9

Peak systemic flow velocity (cm/s): deep cavernosal artery

| Patient #/ Test # | Formulation # | Baseline | 0–15 min | 16–30 min | 31–45 min | 46–60 min |
|---|---|---|---|---|---|---|
| 1/1 | 8-$PGE_1$ | 0 | 0 | 5 | 10 | 8 |
| 1/2 | 8-Placebo | 0 | 0 | 0 | 0 | 0 |
| 2/1 | 8-$PGE_1$ | 0 | 0 | 0 | 15 | 14 |
| 2/2 | 11-$PGE_1$ | 0 | 10 | 17 | 20 | 22 |
| 3/1 | 11-$PGE_1$ | 0 | 0 | 8 | 13 | 9 |
| 3/2 | 13-$PGE_1$ | 0 | 0 | 0 | 0 | 0 |
| 4/1 | 11-$PGE_1$ | 10 | 18 | 17 | 32 | 16 |
| 4/2 | 11-MSC | 0 | 12 | 10 | 10 | 18 |
| 5/1 | 13-$PGE_1$ | 0 | 0 | 0 | 0 | 0 |
| 5/2 | 11-$PGE_1$ | 0 | 0 | 0 | 6 | 6 |

0 No ultrasonographically detectable flow.
MSC Methylsalicylate

Other possible uses for topically applied liposomal $PGE_1$ include the preparation of transdermal formulations for the treatment of impotence as well as the preparation of dermal formulations for the treatment of various skin conditions such as atopic skin, psoriasis, peripheral vascular diseases, wound healing and ischaemic lesions.

TOPICAL LIPOSOME-ENCAPSULATED INTERFERON ALPHA FOR THE TREATMENT OF GENITAL PAPILLOMAVIRUS INFECTIONS

Methods

Liposome preparation

The method used in A. was also used to incorporate IFN alpha which is included in the aqueous phase which is used to hydrate the proliposome gel by mixing at a temperature not exceeding 40° C.

In situ hybridization

For the determination of the presence of HPV DNA (types 6 and 11, types 16 and 18, and types 31, 33, and 35) in paraffin-embedded tissue sections from biopsies of patients, ViraType™ in situ Human Papillomavirus Tissue Hybridization Kit (Life Technologies, Inc., Gaithersburg, Md.) was used.

Immunostaining

Biopsy sections before and after treatment with liposomal IFN alpha were immunostained for the presence of absorbed IFN by using mouse anti-human IFN monoclonal antibody (Boehringer Mannheim Biochemica) and alkaline phosphatase labelled secondary antibody in the form of AS/AP™ universal Mouse Immunostaining Kit (BIO/CAN Scientific Inc., Mississauga, Ont.).

Clinical study

The first patient was a 30-year old female with a three-year history of recurrent genital HPV with cervical involvement (CIN I). On examination prior to instituting topical IFN alpha (F#2) therapy, large confluent plaques and separate verrucous and filiform papules typical for condylomata acuminata were present on the labia majora, labia minora and upper thighs. Histopathology showed condyloma with mild intraepithelial atypia. VIRA-PAP was positive for HPV 6/11. In situ hybridization showed positivity for HPV 6/11, faint reactivity for HPV 31, 33 and 35, negative for HPV 16/18. Treatment protocol was as follows $3\times10^6$ IU/week liposome encapsulated Intron A for 12 weeks, then $10\times10^6$ IU/week for 6 weeks; 1 g twice a day externally, and 1 g once a day intravaginally. The second patient was a 23-year old male with a two-year history of genital HPV. On examination there were multiple flat flesh-colored papules scattered over the shaft, foreskin and glans of the penis. Almost all of the lesions were acetowhite after five minutes of acetic acid soaking. Histopathology showed acanthosis, koilocytes, inflammation. VIRA-PAP was positive for HPV 6/11, negative for HPV 16/18, 31, 33 and 35. In situ hybridization was negative for 6/11; 16/18; 31, 33 and 35. Treatment protocol $3\times10^6$ IU/week liposome encapsulated Intron A for 8 weeks, 1 g twice a day externally. Assessment in both cases was carried out by monitoring the size and number of lesions, histopathology and in situ hybridization.

Results

Cutaneous penetration of $^{125}$I-IFN

The absorption of IFN from various liposomal formulations into human breast skin in vitro was investigated using iodinated IFN as a label. The range of concentration of IFN investigated was 20–80 MU/g preparation. The usual applied dose was 0.1 g preparation/0.32 $cm^2$ skin surface area in the diffusion cell, which corresponds to about 6–28 MU IFN per $cm^2$ skin surface area depending on the concentration tested. The experiments utilized human breast skin from mammoplasty.

Details of formulation of liposomal products containing interferons and intended for topical application are given in Table 10.

TABLE 10

Formulation of topical liposomal IFN products.

| NO. | PRODUCT Lipid phase mg/g product | | Aqueous phase $\mu$l/g product | METHOD OF MANUFACTURE | ENCAPSULATION EFFICIENCY* |
|---|---|---|---|---|---|
| 1 | Phospholipon 90H | 70 | 10.48 IFN stock | Fusion | 55.9 ± 1.5% |
| | Cholesterol | 18 | | | |

TABLE 10-continued

Formulation of topical liposomal IFN products.

| NO. | PRODUCT Lipid phase mg/g product | | Aqueous phase μl/g product | METHOD OF MANUFACTURE | ENCAPSULATION EFFICIENCY* |
|---|---|---|---|---|---|
| | Stearic acid | 18 | (20 × $10^6$ IU) | | |
| | Propylene glycol | 70 | $H_2O$ q.s. | | |
| 2 | Phospholipon 90H | 70 | 10.48 IFN stock | Solvent evaporation | 57.8% |
| | Cholesterol | 18 | | | |
| | Stearic acid | 18 | (20 × $10^6$ IU) | | |
| | Propylene glycol | 70 | $H_2O$ q.s. | | |
| 3 | Phospholipon 90H | 100 | 10.48 IFN stock | Fusion | 57.3% |
| | Cholesterol | 18 | | | |
| | Oleic acid | 6 | (20 × $10^6$ IU) | | |
| | Stearic acid | 6 | $H_2O$ q.s. | | |
| | Erucic acid | 6 | | | |
| | Ascorbyl palmitate | 0.5 | | | |
| | Propylene glycol | 70 | | | |
| 4 | Phospholipon 90 | 200 | 5.24 IFN stock | Fusion | |
| | Ascorbyl palmitate | 1 | $H_2O$ q.s. | | |
| 5 | Phospholipon 90H | 100 | 10.48 IFN stock | Fusion | 59.2% |
| | Cholesterol | 20 | | | |
| | Stearic acid | 10 | (20 × $10^6$ IU) | | |
| | Bovine brain extract | | $H_2O$ q.s. | | |
| | Type VIII | 5 | | | |
| | Propylene glycol | 70 | | | |
| 6 | Phospholipon 90H | 50 | 10.48 IFN stock | Fusion | 69.8 ± 2.3% |
| | Phospholipon 90 | 50 | | | |
| | Cholesterol | 20 | (20 × $10^6$ IU) | | |
| | Bovine brain extract | | $H_2O$ q.s. | | |
| | Type III | 10 | | | |
| | Propylene glycol | 70 | | | |
| 7 | Phospholipon 90H | 50 | 10.48 IFN stock | Fusion | 65.9% |
| | Phospholipon 90 | 50 | | | |
| | Cholesterol | 20 | (20 × $10^6$ IU) | | |
| | Stearylamine | 10 | PBS q.s. | | |
| | Propylene glycol | 70 | | | |
| 8 | Phospholipon 90H | 50 | 10.48 IFN stock | Fusion | 79.0% |
| | Phospholipon 90 | 50 | | | |
| | COMPOUND A | 20 | (20 × $10^6$ IU) | | |
| | Cholesterol | 20 | PBS q.s. | | |
| | Propylene glycol | 70 | | | |
| 9 | Phospholipon 90H | 50 | 10.48 IFN stock | Fusion | 77.8 ± 1.3% |
| | Phospholipon 90 | 50 | | | |
| | COMPOUND A | 10 | (20 × $10^6$ IU) | | |
| | Cholesterol | 20 | PBS q.s. | | |
| | Propylene glycol | 70 | | | |
| 10 | Phospholipon 90H | 100 | 10.48 IFN stock | Fusion | 47.0 ± 1.3% |
| | COMPOUND B | 20 | | | |
| | Cholesterol | 20 | (20 × $10^6$ IU) | | |
| | Propylene glycol | 70 | PBS q.s. | | |
| 11 | Phospholipon 90H | 100 | 10.48 IFN stock | Fusion | 75.2% |
| | COMPOUND A | 10 | | | |
| | COMPOUND B | 10 | (20 × $10^6$ IU) | | |
| | Cholesterol | 20 | PBS q.s. | | |
| | Propylene glycol | 70 | | | |
| 12 | Phospholipon 90H | 50 | 10.48 IFN stock | Fusion | 45.7% |
| | Phospholipon 90 | 50 | | | |
| | COMPOUND B | 10 | (20 × $10^6$ IU) | | |
| | Cholesterol | 20 | PBS q.s. | | |
| | Propylene glycol | 70 | | | |
| 13 | Phospholipon 90 | 100 | 10.48 IFN stock | Fusion | 73.1% |
| | COMPOUND A | 20 | | | |
| | Cholesterol | 20 | (20 × $10^6$ IU) | | |
| | Propylene glycol | 70 | PBS q.s. | | |
| 14 | Phospholipon 90H | 100 | 10.48 IFN stock | Fusion | 54.8% |
| | Centrolex P | 10 | | | |
| | Cholesterol | 20 | (20 × $10^6$ IU) | | |
| | Propylene glycol | 70 | PBS q.s. | | |

*encapsulation efficiency measurerments are the average of 2–5 separate experiments
COMPOUND A = dipalmitoyllysine
COMPOUND B = monolauroyllysine

TABLE 11

Properties of liposomes containing IFN alpha.

| Product No. | Organoleptic properties | Stability* | Microscopy/liposome size distribution |
|---|---|---|---|
| 1 | white cream, homogeneous | (7) | MLV, 1–30 μm, aggregation, fusion |
| 2 | white cream, homogeneous | (7) | MLV, 1–10 μm, even distribution of liposomes, no fusion or aggregation |
| 3 | white lotion, homogeneous | (7) | MLV, 1–10 μm, even distribution of liposomes, no aggregation or fusion |
| 4 | yellow liquid, not appealing | | no liposomes formed |
| 5 | white soft cream, homogeneous | (5) | MLV, 1–15 μm, even distribution of liposomes, some fusion, no aggregation |
| 6 | yellowish-white lotion, homogeneous | (5) | MLV, 1–15 μm, even distribution of liposomes, some fusion, no aggregation |
| 7 | yellowish-white cream, homogeneous | (5) | MLV, 1–15 μm, signs of phase separation, no aggregation or fusion |
| 8 | white cream, homogeneous | (8) | MLV, 1–5 μm, even distribution of liposomes, no fusion or aggregation |
| 9 | white viscous cream, homogeneous | (8) | MLV, 1–5 μm, even distribution of liposomes, no fusion or aggregation |
| 10 | white liquid, not homogeneous | (1) | MLV, 1–20 μm, aggregation, amorphous particles are present |
| 11 | white soft cream, homogeneous | (6) | MLV, 1–10 μm, signs of phase separation, some fusion, no aggregation, few amorphous particles are present |
| 12 | white liquid, homogeneous | (6) | MLV, 1–5 μm, signs of phase separation, some fusion, no aggregation, amorphous particles are present |
| 13 | white lotion, not homogeneous | (6) | Liposomes? or emulsion? , amorphous particles and membrane fragments are present |
| 14 | white lotion, homogeneous | (5) | MLV, 1–20 μm, aggregation, fusion, signs of phase separation |

*Stability of liposomes was evaluated after 1 month according to the following rating scale:
Visual stability rating for disperse system products (S. A. Hanna, 1989)
9 No visual separation, completely homogeneous
8 No visual separation, virtually homogeneous
7 Very indistinct separation, no clear layer at bottom or top
6 Indistinct separation, no clear layer at bottom or top
5 Distinct separation, no clear layer at bottom or top
4 Homogeneous top or bottom layer, clear layer at bottom or top
3 Distinct separation, clear layer at bottom or top with no coalescence
2 Distinct separation with slight coalescence
1 Distinct separation with slight coalescence
0 Complete separation and complete coalescence The products described in Tables 10 and 11 were subjected to various tests and results are given below.

The cutaneous penetration of IFN from various liposomal formulas containing 20 MU/g preparation are shown in Tables 12 and 13.

TABLE 12

Cutaneous absorption of $^{125}$X-IFN from liposomal formulations at 48 h steady state. The total amount of IFN in whole skin (all skin layers together) is presented

| | |
|---|---|
| Drug concentration in product: | $20 \times 10^6$ IU IFN/g product |
| Dose/unit skin surface area: | $6 \times 10^6$ IU IFN/cm$^2$ |
| Skin used: | 0716-92 |
| Tracer: | $^{125}$I-IFN |
| Duration of experiment: | 48 h |
| The values represent the mean ± S.D. | (n = 4) |

TABLE 12-continued

Cutaneous absorption of $^{125}$X-IFN from liposomal formulations at 48 h steady state. The total amount of IFN in whole skin (all skin layers together) is presented

| | IFN in WHOLE skin | | |
|---|---|---|---|
| PRODUCTS* | ng/cm$^2$ | IU/cm$^2$ | % of total applied |
| F#2 | 491.75 ± 136.39 | 110,380 ± 30.615 | 2.00 ± 0.55 |
| F#3 | 1004.84 ± 269.18 | 225,553 ± 60,424 | 3.47 ± 0.93 |
| F#5 | 783.67 ± 52.49 | 175,904 ± 11,783 | 2.70 ± 0.18 |
| F#9 | 971.29 ± 157.52 | 218,022 ± 35.358 | 3.32 ± 0.54 |
| F#10 | 822.58 ± 202.53 | 183,022 ± 45,120 | 3.56 ± 0.88 |
| F#11 | 768.11 ± 151.44 | 172,409 ± 33,992 | 3.16 ± 0.62 |
| Solution | 344.41 ± 105.52 | 77,306 ± 23,684 | 1.23 ± 0.38 |

*See Table 10 above for components of these liposomal formulations.

TABLE 13

Cutaneous absorption of $^{125}$I-IFN from liposomal formulations at 48 h steady state. The amount of IFN in the stratum corneum and in the deeper layers of skin (viable epidermis and dermis) is presented.

| | |
|---|---|
| Drug concentration in product: | 20 × $10^6$ IU IFN/g product |
| Dose/unit skin surface area: | 6 × $10^6$ IU IFN/cm$^2$ |
| Skin used: | 0716-92 |
| Tracer: | $^{125}$I-IFN |
| Duration of experiment: | 48 h |
| The values represent the mean ± S.D. | (n = 4) |

| | IFN in stratum corneum | | | IFN in viable epidermis + dermis | | |
|---|---|---|---|---|---|---|
| PRODUCTS | ng/cm$^2$ | IU/cm$^2$ | % of total | ng/cm$^2$ | IU/cm$^2$ | % of total |
| F#2 | 239.63 ± 136.39 | 53,787 ± 28,833 | 0.95 ± 0.51 | 213.90 ± 33.04 | 48,013 ± 74.15 | 0.87 ± 0.13 |
| F#3 | 331.15 ± 111.04 | 74,346 ± 24,929 | 1.14 ± 0.38 | 690.86 ± 326.07 | 155,076 ± 73,191 | 2.38 ± 1.12 |
| F#5 | 375.57 ± 183.82 | 84,308 ± 41,263 | 1.29 ± 0.63 | 426.95 ± 211.60 | 95,833 ± 47,495 | 1.47 ± 0.73 |
| F#9 | 554.07 ± 188.27 | 124,343 ± 42,250 | 1.94 ± 0.66 | 528.65 ± 202.55 | 118,665 ± 45,467 | 1 85 ± 0.71 |
| F#10 | 426.17 ± 192.54 | 95,750 ± 43,260 | 1.85 ± 0.83 | 418.26 ± 78.44 | 93,180 ± 17.475 | 1.81 ± 0.34 |
| F#11 | 485.26 ± 228.59 | 108.955 ± 51,324 | 1.99 ± 0.94 | 322.52 ± 72.93 | 72,393 ± 16,369 | 1.32 ± 0.30 |
| Solution | 155.06 ± 65.61 | 34,815 ± 14,730 | 0.56 ± 0.23 | 178.14 ± 23.40 | 39,985 ± 5,257 | 0.64 ± 0.08 |

With the dosage regimen used in this study the applied dose was around 6 MU/cm$^2$. The absorption of IFN from the various liposomal formulas was fairly similar, 2.00–3.56% of the total applied when the whole (unstripped skin was analyzed (Table 12). This corresponds to about 110, 000–218,000 IU IFN/cm$^2$ skin. When the stripped skin was analyzed (Table 13), the difference in the rate of absorption into the deeper layers, i.e. the viable epidermis and dermis, was noticeable. The amount of IFN delivered by Products #3, 5, 9, 10 and 11 was in the range of 72,000–155,000 IU/cm$^2$. The control IFN solution at the same concentration and dose delivered approximately 77,000 IU IFN/cm$^2$ into 'whole' skin (1.23±0.38% of total applied) and 40,000 IU/cm$^2$ into the deeper layers of skin (0.64%±0.08 of total). Similar results were obtained when more concentrated solutions were used.

Upon increasing the dose the amount of IFN absorbed also increased. Selected formulas with 40 MU/g were prepared and tested. In this case the applied dose was around 12 MU/cm$^2$. F#5-40, F#10-40 and F#11-40 had the same lipid composition as before except the initial drug concentration was increased. The amount of absorbed IFN into skin reached about 0.5 MU/cm$^2$.

Table 14 indicates that among these three preparations F#10-40 delivered the highest amount of IFN, close to 600, 000 IU/cm$^2$. After stripping the skin the level of IFN in the skin treated with Product #10-40 was still close to 0.5 MU/cm$^2$. F#5-40 and F#11-40 delivered somewhat lower quantities of IFN into the deeper layers of the skin.

TABLE 14

Cutaneous absorption of $^{125}$IN-IFN from liposomal formulas containing 40 MU/g IFN at 48 h steady state. The amount of IFN in whole skin (all skin layers together) and in the stratum corneum and in the deeper layers of skin are presented.

| | |
|---|---|
| Drug concentration in product: | 40 × $10^6$ IU IFN/g product |
| Dose/unit skin surface area: | 12 × $10^6$ IU IFN/cm$^2$ |
| Skin used. | 0716-92 |
| Tracer: | $^{125}$I-IFN |
| Duration of experiment: | 48 h |
| The values represent the mean ± S.D. | (n = 4) |

TABLE 14-continued

Cutaneous absorption of $^{125}$IN-IFN from liposomal formulas containing 40 MU/g IFN at 48 h steady state. The amount of IFN in whole skin (all skin layers together) and in the stratum corneum and in the deeper layers of skin are presented.

| | IFN in WHOLE skin | | |
|---|---|---|---|
| PRODUCTS | ng/cm$^2$ | IU/cm$^2$ | % of total applied |
| F#5-40 | 1560.63 ± 157.68 | 350,309 ± 35,395 | 3.37 ± 0.34 |
| F#10-40 | 2627.28 ± 705.42 | 589,284 ± 158,221 | 4.69 ± 1.26 |
| F#11-40 | 1830.23 ± 625.73 | 409,837 ± 140,118 | 3.40 ± 1.16 |
| | IFN in stratum corneum | | |
| PRODUCTS | ng/cm$^2$ | IU/cm$^2$ | % of total |
| F#5-40 | 808.10 ± 296.25 | 181,459 ± 66,523 | 1.74 ± 0.64 |
| F#10-40 | 460.02 ± 282.00 | 103,176 ± 63,250 | 0.82 ± 0.50 |
| F#11-40 | 952.06 ± 352.05 | 213,244 ± 78,851 | 1.77 ± 0.65 |
| | IFN in viable epidermis-dermis | | |
| PRODUCTS | ng/cm$^2$ | UI/cm$^2$ | % of total |
| F#5-40 | 734.12 ± 174.67 | 164,785 ± 39,207 | 1.58 ± 0.37 |
| F#10-40 | 2141.61 ± 959.46 | 480,350 ± 215,202 | 3.82 ± 1.71 |
| F#11-40 | 930.59 ± 676.30 | 208,385 ± 151,441 | 1.72 ± 1.25 |

With F#5 and F#10 the concentration of IFN was further increased to 80 MU/g to determine whether more drug can be delivered. Table 15 below shows that F#10-80 delivered close 0.9 MU/cm$^2$ into the skin. The viable epidermis and dermis contained about 0.7 MU/cm$^2$. It is noteworthy that F#10 in general delivered a greater proportion of IFN into the deeper layers of the skin. This effect is more pronounced at 40 MU/g and at 80 MU/g product concentration (Tables 14 and 15). Estimation of antiviral activity in skin treated with liposomal IFN alpha.

TABLE 15

Cutaneous absorption of $^{125}$IN-IFN from liposomal formulas containing 80 MU/g IFN at 48 h steady state. The amount of IFN in whole skin (all skin layers together) and in the stratum corneum and in the deeper layers of skin are presented.

| | |
|---|---|
| Drug concentration in product: | 80 × $10^6$ IU IFN/g product |
| Dose/unit skin surface area: | 28 × $10^6$ IU IFN/cm$^2$ |
| Skin used: | 0716-92 |

TABLE 15-continued

Cutaneous absorption of $^{125}$IN-IFN from liposomal formulas containing 80 MU/g IFN at 48 h steady state. The amount of IFN in whole skin (all skin layers together) and in the stratum corneum and in the deeper layers of skin are presented.

Tracer: $^{125}$I-IFN
Duration of experiment: 48 h
The values represent the mean ± S.D. (n = 4)

| | IFN in WHOLE skin | | |
|---|---|---|---|
| PRODUCTS | ng/cm$^2$ | IU/cm$^2$ | % of total applied |
| F#5-80 | 3452.49 ± 929.00 | 773,106 ± 208,028 | 2.75 ± 0.74 |
| F#10-80 | 3867.71 ± 1375.89 | 866,084 ± 308,099 | 3.21 ± 1.41 |
| | IFN in stratum corneum | | |
| PRODUCTS | ng/cm$^2$ | IU/cm$^2$ | % of total |
| F#5-80 | 1976.43 ± 1575.20 | 442,587 ± 352,728 | 1.57 ± 1.25 |
| F#10-80 | 728.19 ± 610.93 | 163,058 ± 136,800 | 0.60 ± 0.50 |
| | IFN in viable epidermis-dermis | | |
| PRODUCTS | ng/cm$^2$ | IU/cm$^2$ | % of total |
| F#5-80 | 1216.18 ± 370.58 | 272,335 ± 82,983 | 0.97 ± 0.29 |
| F#10-80 | 3080.23 ± 1196.41 | 689,746 ± 267,210 | 2.55 ± 0.99 |

Measuring cutaneous penetration by radioactivity is an efficient way of comparing several different formulations and calculate approximate levels of protein in the skin. However, this method cannot answer the question whether the protein absorbed is intact and active.

In order to get a better understanding whether the radioactive label represents active protein, antiviral assays with the skin samples treated with liposomal IFN (20 MU/g) were carried out. These antiviral assays indicated that there was antiviral activity in the skin with each liposomal formula tested (Table 16, below). The values obtained by antiviral assay were about ten times lower than the amount of IFN detectable in skin by the radioactive method for all formulas except F#10. In case of F#10 the antiviral activity corresponded well with the result from the radioactive experiments (compare Table 12 and Table 16).

TABLE 16

Estimation of antiviral activity in skin treated with liposomal IFN alpha in vitro

| Product Number | Total IFN in breast skin at 48 h (IU/cm$^2$) |
|---|---|
| F#2 | 17,200 |
| F#3 | 26,600 |
| F#5 | 21,900 |
| F#10 | 219,000 |
| F#9 | 17,200 |
| F#11 | 17,200 |
| IFN solution | 12,000 |

Delivery of IFN alpha into surgically removed genital wart tissue

Excised condyloma tissues were treated with low-dose liposomal IFN (F#10-80) to obtain preliminary information about the rate of drug delivery. The difficulty of in vitro experiments with wart tissues is the localization of adequate quantities of product on the surface of the lesions. The two dose regimens used (0.5 MU/lesion and 2 MU/lesion, approximately) was required to form a sufficiently thick layer of the product on the surface of the tissue and any additional amount would not be accommodated (it would fall off). The results of these experiments are shown in Table 17, below.

Seven excised condyloma lesions (average diameter 5 mm) were treated with an average of 0.5 MU dose of F#10-80. The amount of IFN delivered into the lesions was 34,400±18,100 IU (6.5% of the total amount applied). After determining the radioactivity in the 'whole' lesions (i.e. after thorough washing and blotting of the warts), the outer layers were removed by tape stripping and the radioactivity remaining in the deeper layers was determined. The average amount of IFN in the deeper layer was 29,000±15,300 IU (5.5% of the total amount applied).

Three condyloma lesions were used for the experiments with the higher dose (2 MU/lesion) treatment. The total amount of IFN delivered was 323,500±235,100 IU (14.8% of total) and the remaining radioactivity after stripping of the warts was 286,500±208,900 IU (9.5% of total).

These experiments show potential for this formulation to deliver sufficient quantities of drug. However, by improving the experimental set up a better estimation of the delivery rate into wart tissue could be obtained. Some of the difficulties in these experiments are the availability of tissues of similar sizes, the application of the liposome cream to the lesions, the incubation set-up and the analysis of the tissues.

Treatment of patients with liposome encapsulated IFN alpha (F#2)

After several weeks of therapy of the female patient there was softening and thinning of the condyloma and also lightening of the hyperpigmentation. Three lesions removed under local anesthesia from the right upper thigh at tenth week of therapy were still resolved at the end of a 12-week course of liposomal interferon treatment and the area continued to show no sign of recurrence seven weeks after removal. Colposcopy one month following discontinuation of liposomal interferon therapy showed no evidence of HPV involvement of the cervix. In case of the male patient, several lesions on the distal foreskin and glans resolved after two weeks of liposomal interferon twice a day. Multiple lesions remained after eight weeks of therapy, when the patient moved from the area and was lost to follow-up. The lesions which resolved within the first two weeks remained gone during the observation period.

The pretreatment biopsy sections were not greatly different from the post-treatment sections, both showing acanthosis and papillomatosis, however koilocytic changes were less apparent in the post-treatment sections. In situ hybridization of tissue sections obtained by biopsy 18 week post-treatment of the female patient showed only a relatively weak, focal staining for HPV 6 and 11 in rare superficial cells as opposed to pretreatment, when the test showed numerous foci of positively staining nuclei within superficial layers of the epithelium. These latter results might indicate the elimination of HPV virus from the wart tissues.

We conclude that liposomes are a suitable delivery system for IFN alpha and a dermatologically acceptable dosage form. Our preliminary clinical studies indicate the efficacy of topically applied liposome encapsulated IFN alpha in the treatment of genital HPV infections.

TABLE 17

Treatment of excised condyloma tissues with low-dose topical liposomal IFN alpha (F#10-80) for 24 h.

| Condyloma lesion # | Size ϕ (mm) | Weight | Surface area ($cm^2$) | IFN applied (IU) | IFN in WHOLE lesion (IU) | IFN in deeper layers (IU) |
|---|---|---|---|---|---|---|
| DOSE REGIMEN I: | | | | | | |
| 1 | 5 | 0.0794 | 0.78 | 560,000 | 29,800 | 25,700 |
| 2 | 4 | 0.0509 | 0.50 | 496,000 | 31,500 | 29,200 |
| 3 | 7 | 0.0542 | 1.54 | 864,000 | 18,100 | 13,100 |
| 4 | 4.5 | 0.0788 | 0.64 | 432,000 | 70,700 | 57,800 |
| 5 | 5 | 0.0807 | 0.78 | 424,000 | 31,000 | 25,300 |
| 6 | 7 | 0.0621 | 1.54 | 240,000 | 17,400 | 13,900 |
| 7 | 6 | 0.0766 | 1.13 | 672,000 | 42,100 | 37,700 |
| Average | 5.5 | 0.0689 | 0.95 | 527,000 | 34,400 ± 18,100 (6.5% of total applied) | 29,000 ± 15,300 (5.5% of total applied) |
| DOSE REGIMEN II: | | | | | | |
| 8 | 6 | 0.0925 | 1.13 | $1.34 \times 10^6$ | 65,300 | 56,700 |
| 9 | 8 | 0.1235 | 2.01 | $2.82 \times 10^6$ | 525,100 | 464,700 |
| 10 | 12 | 0.1845 | 4.52 | $2.42 \times 10^6$ | 380,200 | 338,200 |
| Average | 8.7 | 0.1335 | 2.55 | $2.19 \times 10^6$ | 323,500 ± 235,100 (14.8% of total applied) | 286,500 ± 208,900 (9.5% of total applied) |

What I claim is:

1. A method of preparing liposomes having a central core compartment containing an oil-in-water emulsion, comprising preparing an oil-in-water emulsion stabilized by a surfactant; and mixing said oil-in-water emulsion with vesicle-forming lipids to form liposomes having a lipid-bilayer membrane composed of the vesicle-forming lipids and containing the oil-in-water emulsion in the central core compartment.

2. The method of claim 1, wherein said preparing comprises (i) mixing the water and the surfactant to form a hydrophilic phase; and (ii) blending the hydrophilic phase with a lipophilic phase to obtain a hydrophilic continuous phase and a dispersed lipophilic phase.

3. The method of claim 2, wherein said lipophilic phase consists of lipophilic droplets having a size of less than 0.5 micrometers dispersed in the hydrophilic phase.

4. The method of claim 3, wherein said lipophilic phase is composed of an oil and a compound selected from the group consisting of fatty alcohols, waxes, fatty alcohol, fatty acid esters, glyceride esters, petrolatum and mixtures thereof.

5. The method of claim 1, wherein said vesicle-forming lipid is solubilized in a hydrophilic pharmaceutically acceptable solvent other than water.

6. The method of claim 5, wherein said hydrophilic solvent is selected from the group consisting of propylene glycol, glycerol, polyethylene glycol having a molecular weight between 300–800 daltons, ethanol and mixtures thereof.

7. The method of claim 5, wherein said vesicle-forming lipid is selected from the group consisting of glycolipids, phospholipids, ceramides and mixtures thereof.

8. The method of claim 2, wherein a penetration enhancer is added to the oil-in-water emulsion in either the hydrophilic phase or the lipophilic phase.

9. The method of claim 5, wherein a penetration enhancer is further added to said solubilized vesicle-forming lipid.

10. The method of claim 5, wherein said lipid-bilayer membrane further comprises a compound selected from the group consisting of steroids, long chain fatty acids, fatty amines, fatty acylated proteins, fatty acylated peptides, fatty acylated polyethylene glycol and mixtures thereof.

11. The method of claim 1, wherein said liposomes further comprise a biologically active agent in entrapped form.

12. The method of claim 11, wherein the therapeutic agent is incorporated in the oil-in-water emulsion.

13. The method of claim 12, wherein the therapeutic agent is lipophilic and is added to the lipophilic phase of said emulsion.

14. The method of claim 12, wherein the therapeutic agent is hydrophilic and is added to the hydrophilic phase of said emulsion.

15. The method of claim 11, wherein the therapeutic agent is incorporated in the lipid bilayer membrane.

16. The method of claim 14, wherein said therapeutic agent is interferon alpha.

17. The method of claim 15, wherein said therapeutic agent is prostaglandin E1.

18. The method of claim 1, said surfactant is a cationic surfactant.

19. The method of claim 18, wherein said surfactant is selected from the group consisting of linoleamidopropyl PG-dimonium chloride phosphate, cocamidopropyl PG-dimonium chloride phosphate and stearamidopropyl PG-dimonium chloride phosphate.

20. A method of preparing liposomes having a central core compartment containing an oil-in-water emulsion, comprising preparing an oil-in-water emulsion which is stabilized by a surfactant;

solubilizing a vesicle-forming lipid in a pharmaceutically-acceptable solvent other than water;

adding the oil-in-water emulsion to the solubilized vesicle-forming lipid; and mixing to form liposomes having a lipid-bilayer membrane composed of the vesicle-forming lipid and containing the oil-in-water emulsion in the central core compartment.

21. The method of claim 20, wherein said preparing further comprises the steps of (i) mixing the water and the surfactant to form a hydrophilic phase; and (ii) blending the hydrophilic phase with a lipophilic phase to obtain a hydrophilic continuous phase and a dispersed lipophilic phase.

22. The method of claim 20, wherein said liposomes further comprise a biologically active agent.

* * * * *